(12) United States Patent
Yasuda et al.

(10) Patent No.: US 11,375,982 B2
(45) Date of Patent: Jul. 5, 2022

(54) ULTRASONIC DIAGNOSTIC DEVICE, SIGNAL PROCESSING DEVICE, AND PROGRAM

(71) Applicant: Hitachi, Ltd., Tokyo (JP)

(72) Inventors: Jun Yasuda, Tokyo (JP); Noriaki Inoue, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 107 days.

(21) Appl. No.: 16/823,524

(22) Filed: Mar. 19, 2020

(65) Prior Publication Data
US 2020/0315588 A1  Oct. 8, 2020

(30) Foreign Application Priority Data

Apr. 4, 2019  (JP) .............................. JP2019-072288

(51) Int. Cl.
*A61B 8/08* (2006.01)
*A61B 8/00* (2006.01)

(52) U.S. Cl.
CPC .......... *A61B 8/5223* (2013.01); *A61B 8/4444* (2013.01); *A61B 8/463* (2013.01); *A61B 8/467* (2013.01); *A61B 8/485* (2013.01); *A61B 8/5207* (2013.01); *A61B 8/54* (2013.01); *A61B 8/56* (2013.01)

(58) Field of Classification Search
CPC ........ A61B 8/5233; A61B 8/5207; A61B 8/56
See application file for complete search history.

(56) References Cited

U.S. PATENT DOCUMENTS

| 2013/0278776 | A1* | 10/2013 | Guterman | ................. G06T 7/12 348/163 |
| 2016/0375258 | A1* | 12/2016 | Steinke | ................ A61N 1/3605 607/59 |
| 2017/0296150 | A1* | 10/2017 | Rosenzweig | ....... G01S 7/52022 |

FOREIGN PATENT DOCUMENTS

JP            2018-099180 A        6/2018

OTHER PUBLICATIONS

Reddy, B. Srinivasa, and Biswanath N. Chatterji. "An FFT-based technique for translation, rotation, and scale-invariant image registration." IEEE transactions on image processing 5.8 (1996): 1266-1271.*

* cited by examiner

*Primary Examiner* — Ashley K Buran
*Assistant Examiner* — Sean V Blinder
(74) *Attorney, Agent, or Firm* — Mattingly & Malur, PC

(57) ABSTRACT

A shear wave velocity is accurately measured. Time change data of a displacement of a tissue due to a shear wave generated in a test object is calculated from a reception signal obtained by transmitting an ultrasonic wave to the test object and receiving a reflected wave. The time change data of the displacement is converted into spectrum data indicating a displacement distribution in a frequency space having a spatial frequency and a time frequency as two axes. Spectrum data in a predetermined region is extracted by rotating the spectrum data by a predetermined angle in the frequency space, and filtering the rotated spectrum data. A velocity of the shear wave is calculated based on the extracted spectrum data in the predetermined region.

8 Claims, 27 Drawing Sheets

[FIG. 1]
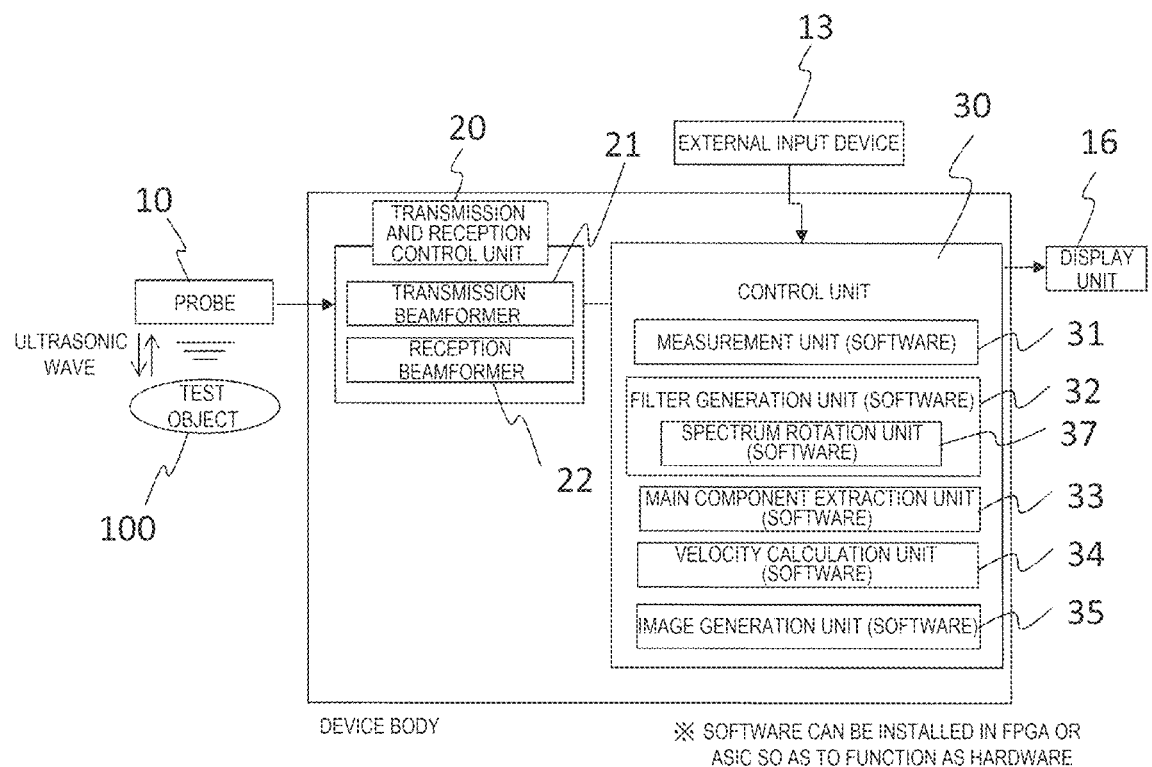

[FIG. 2]
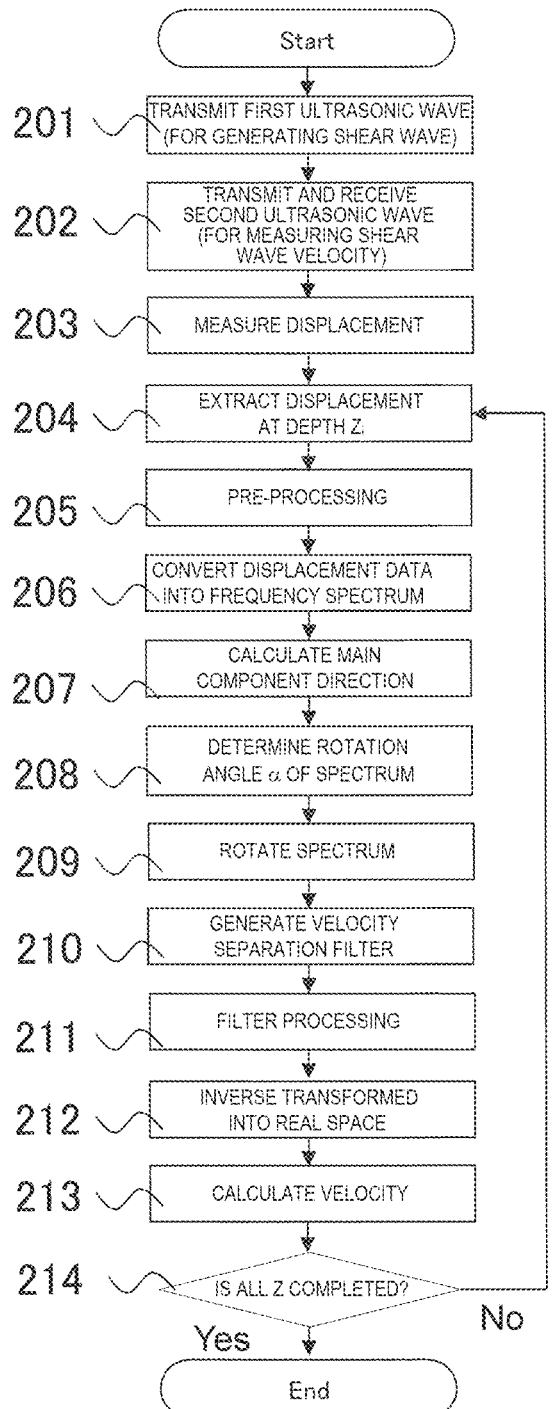

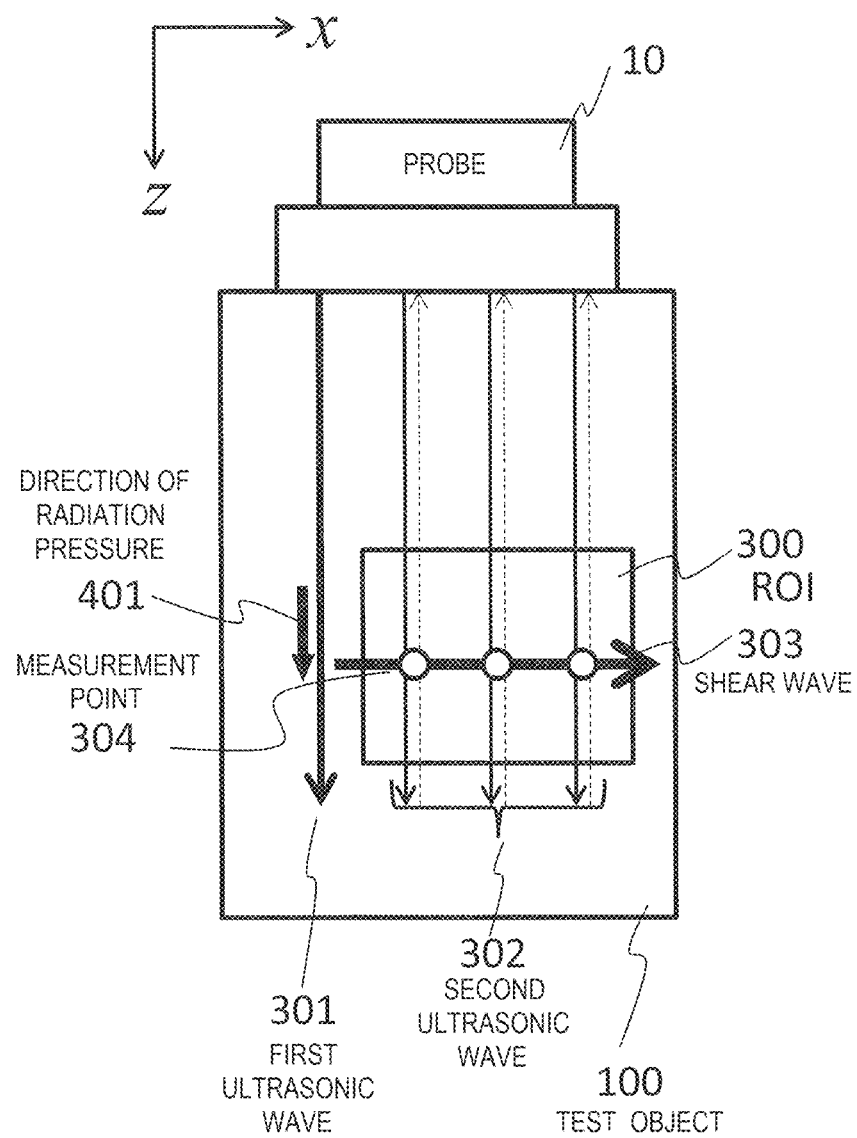
[FIG. 3]

[FIG. 4A]
HOW SHEAR WAVE PROPAGATES
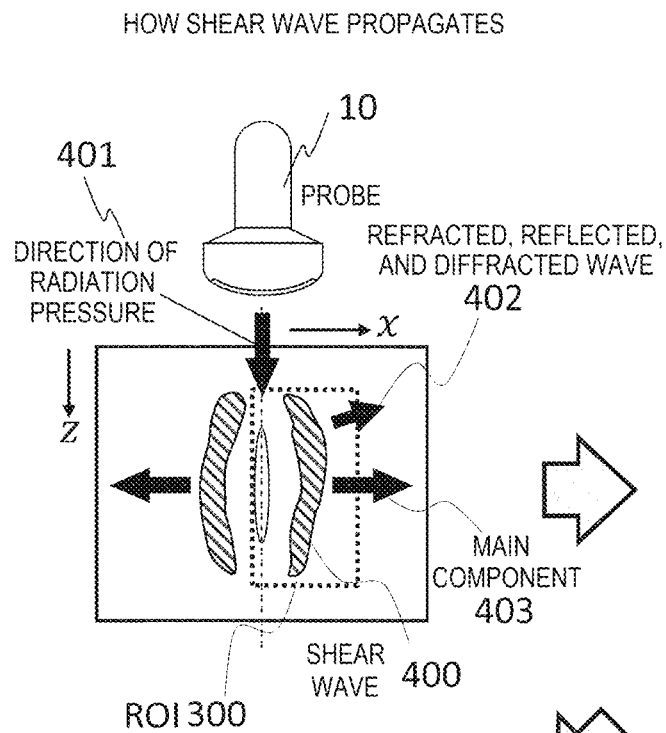
[FIG. 4B]
TIME-SERIES INFORMATION OF DISPLACEMENT DISTRIBUTION IN z-x PLANE
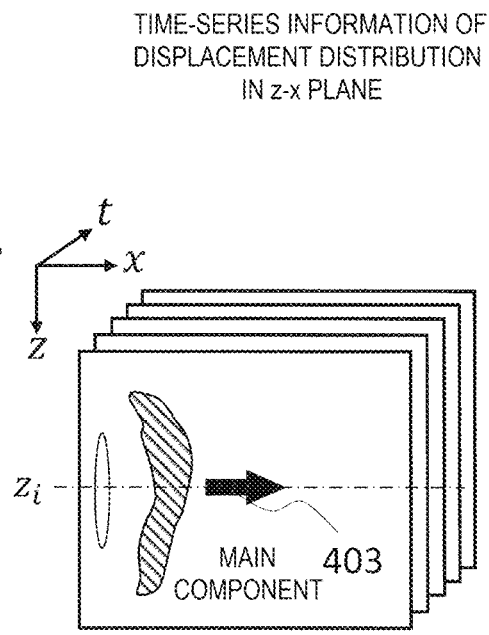
[FIG. 4C]
DISPLACEMENT DISTRIBUTION IN x-t PLANE AT DEPTH $Z_i$
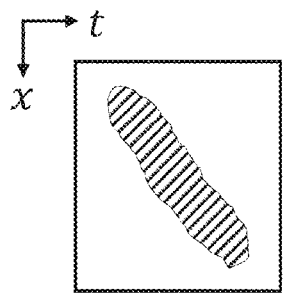

[FIG. 5A]
DISPLACEMENT DISTRIBUTION
IN x-t PLANE
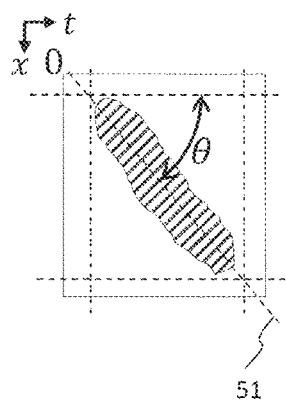
[FIG. 5B]
DISPLACEMENT DISTRIBUTION IN
FREQUENCY SPACE k-f PLANE
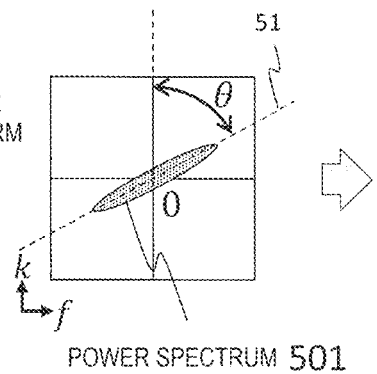
POWER SPECTRUM 501
[FIG. 5C]
FILTER
PROCESSING
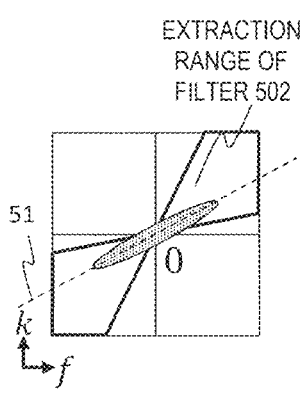
EXTRACTION
RANGE OF
FILTER 502

[FIG. 6A]
CONSTANT VELOCITY LINE ON FREQUENCY SPACE k-f PLANE
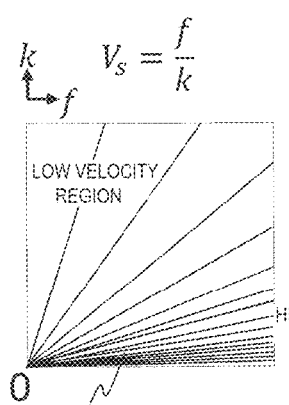
601 CONSTANT VELOCITY LINE
[FIG. 6B]
VELOCITY GRADIENT IN FREQUENCY SPACE k-f PLANE
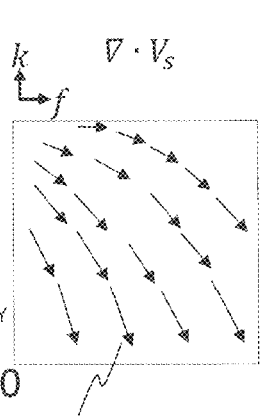
602 GRADIENT VECTOR
[FIG. 6C]
ABSOLUTE VALUE OF VELOCITY GRADIENT IN FREQUENCY SPACE k-f PLANE
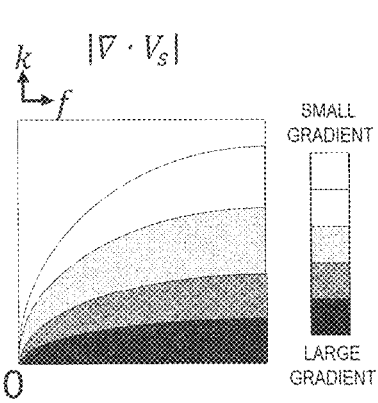
[FIG. 6D]
CONSTANT VELOCITY LINE IN FREQUENCY SPACE k-f PLANE
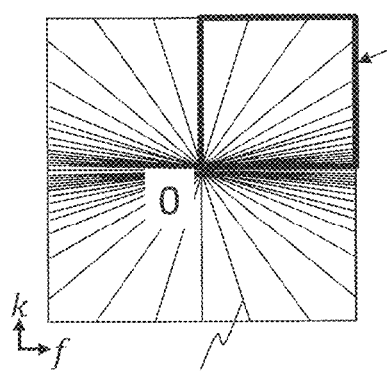
601 CONSTANT VELOCITY LINE
[FIG. 6E]
VELOCITY RANGE PER MESH
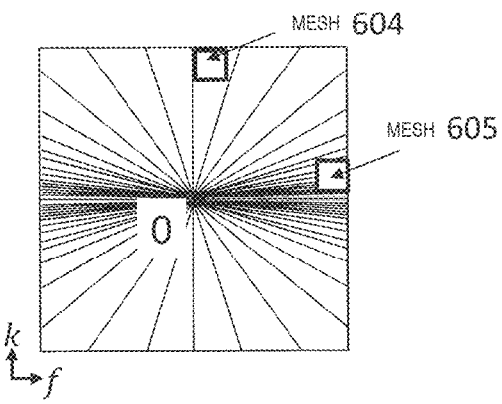

[FIG. 7A]
DISPLACEMENT
DISTRIBUTION IN x-t PLANE
$g_{before}(x, t)$
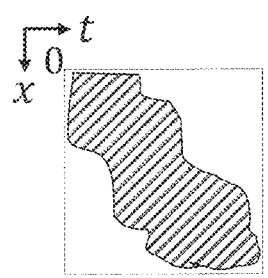
[FIG. 7B]
DISPLACEMENT DISTRIBUTION IN
FREQUENCY SPACE k-f PLANE
$G(k, f)$
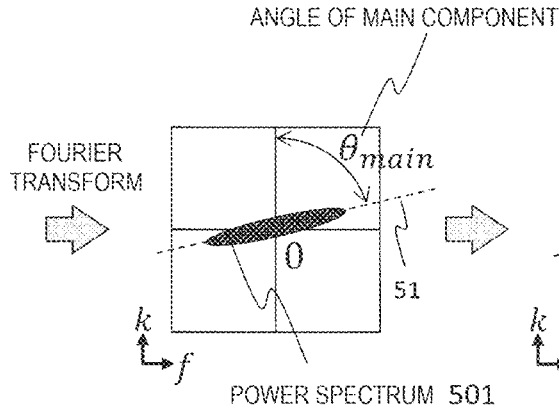
POWER SPECTRUM 501
[FIG. 7C]
ROTATED k-f FREQUENCY
DISTRIBUTION
$G(k, f) \cdot R(\alpha)$
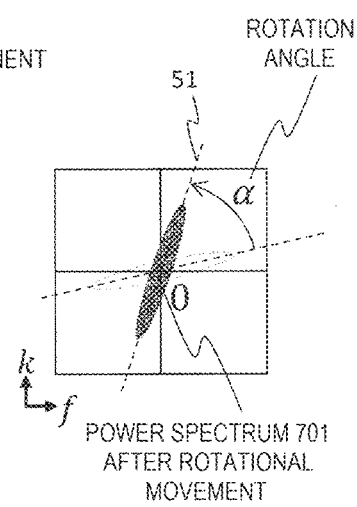
POWER SPECTRUM 701
AFTER ROTATIONAL
MOVEMENT

[FIG. 8A]
DETERMINATION METHOD OF
EXTRACTION ANGLE RANGE OF FILTER
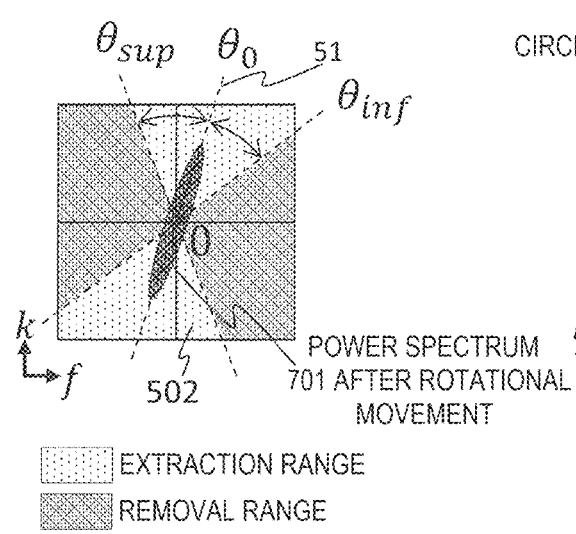
[FIG. 8B]
DETERMINATION METHOD OF
EXTRACTION ANGLE
RANGE OF FILTER
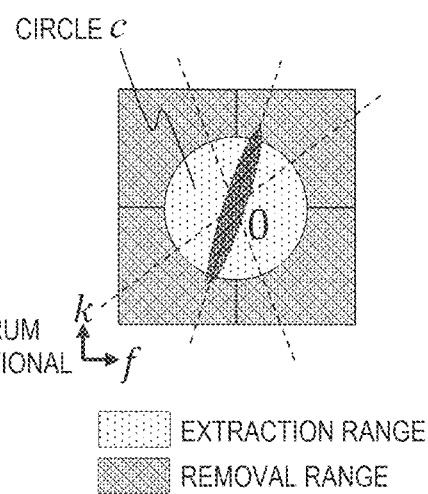
[FIG. 8C]
GENERATED FILTER
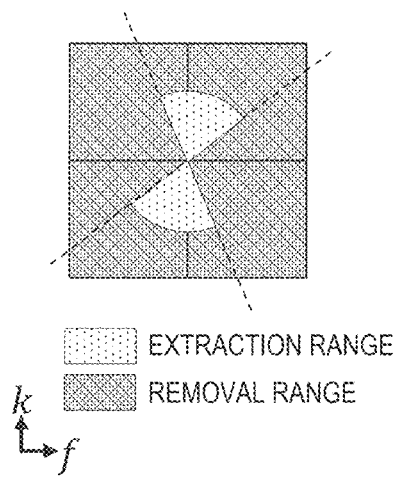

[FIG. 9]
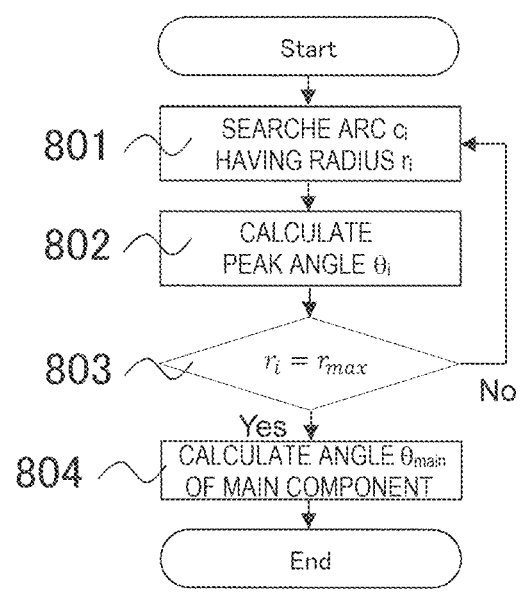

[FIG. 10A]
PEAK VALUE OF DISPLACEMENT IN
FREQUENCY SPACE k-f PLANE
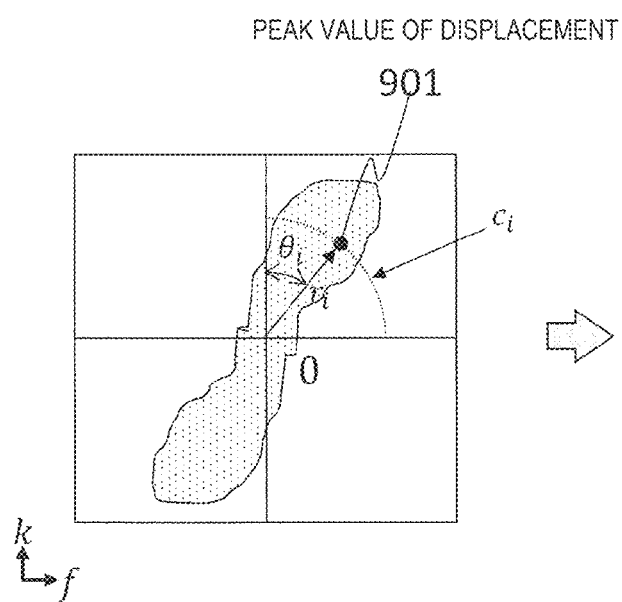
[FIG. 10B]
ANGLE $\theta_{main}$ OF MAIN COMPONENT
IN FREQUENCY SPACE k-f PLANE
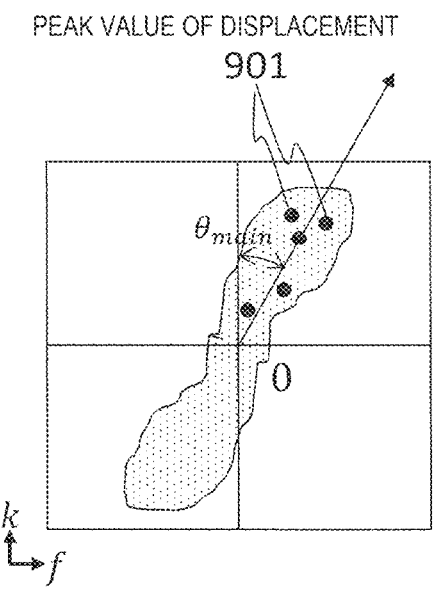

[FIG. 11]
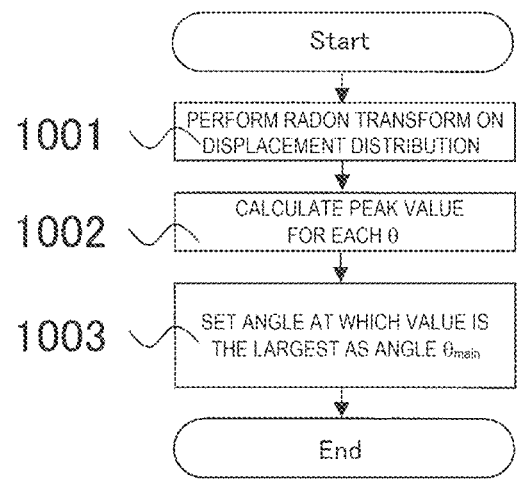

[FIG. 12A]
DISPLACEMENT
DISTRIBUTION IN x-t
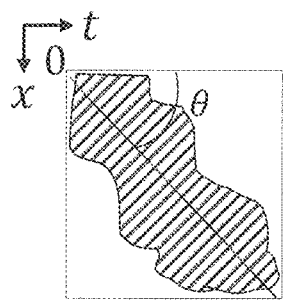
RADON TRANSFORM
[FIG. 12B]
RADON TRANSFORMED
DISPLACEMENT DISTRIBUTION IN x-t
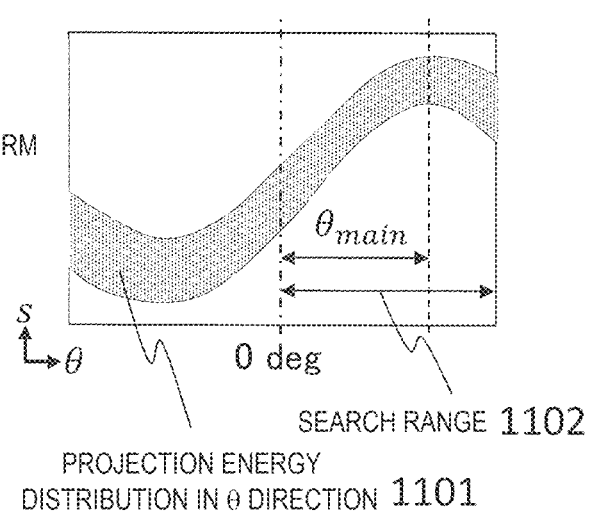
SEARCH RANGE 1102
PROJECTION ENERGY
DISTRIBUTION IN θ DIRECTION 1101

[FIG. 13]
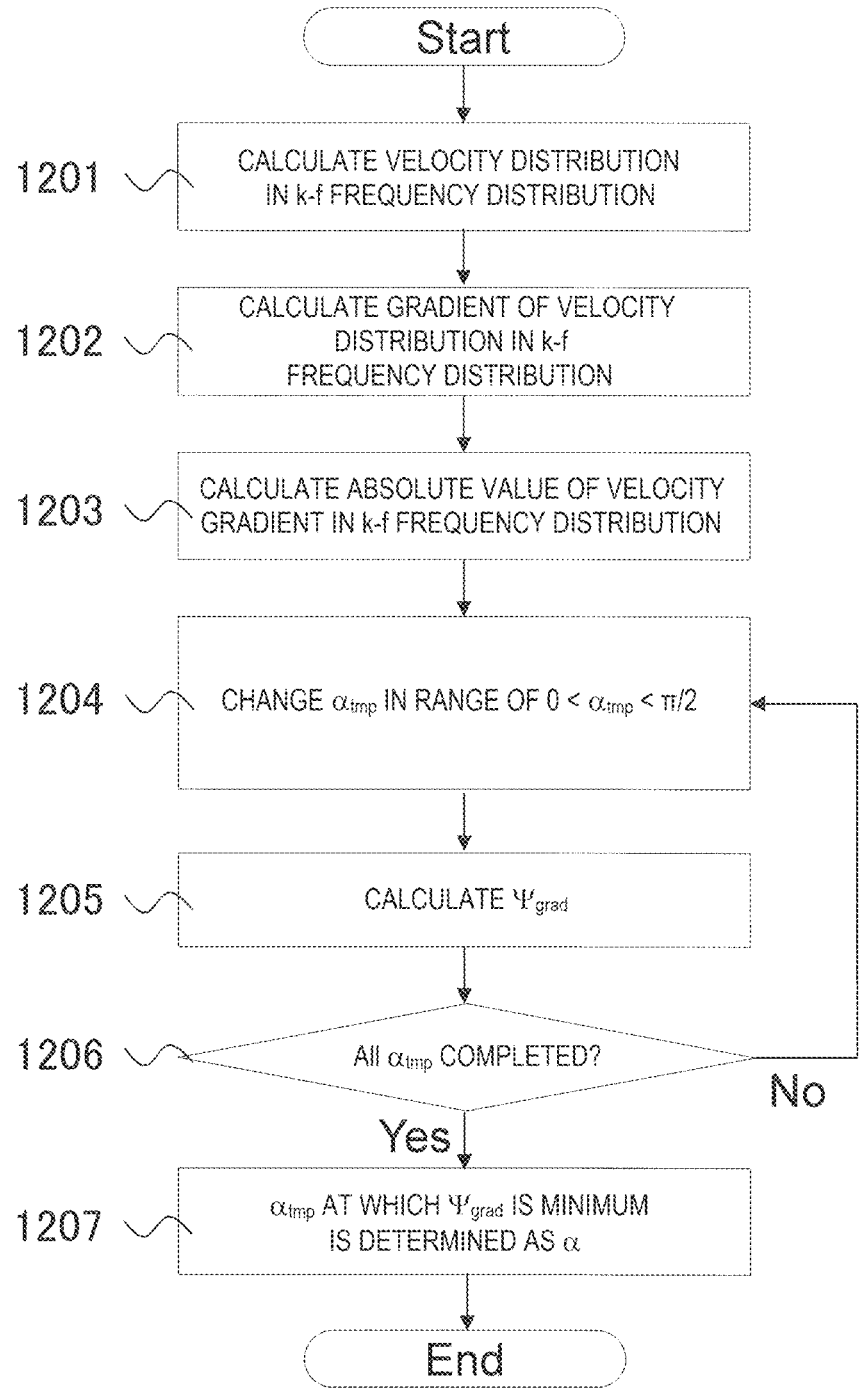

[FIG. 14A]
ABSOLUTE VALUE DISTRIBUTION
OF VELOCITY GRADIENT
$|\nabla \cdot V_s|$
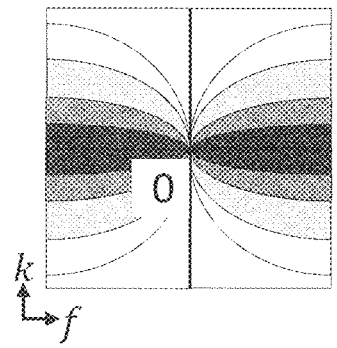
[FIG. 14B]
FREQUENCY DISTRIBUTION IN
k-f SPACE ROTATED BY $\alpha_{tmp}$
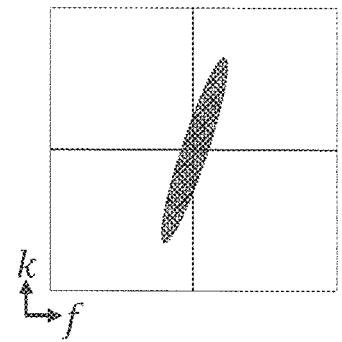

[FIG. 15]
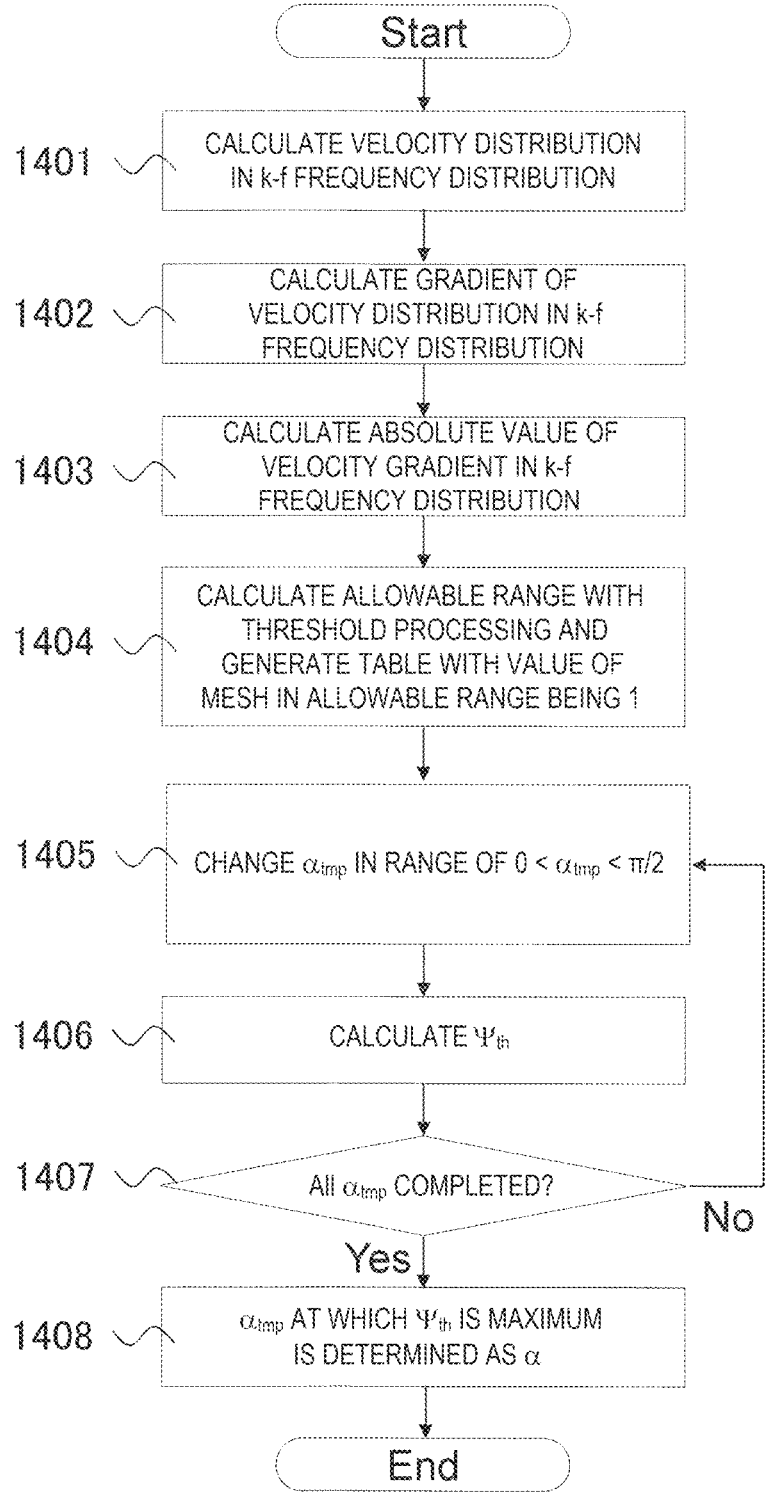

[FIG. 16A]
ABSOLUTE VALUE DISTRIBUTION
OF VELOCITY GRADIENT
(CONTOUR DISPLAY)
$|\nabla \cdot V_s|$
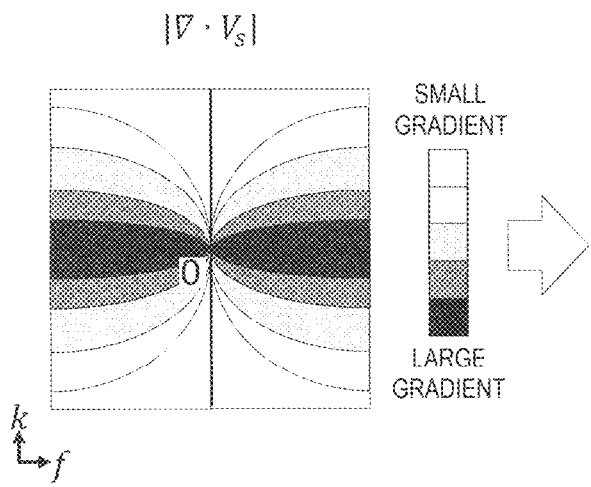
[FIG. 16B]
METHOD FOR DETERMINING
ALLOWABLE RANGE BY THRESHOLD
$P(k, f)$
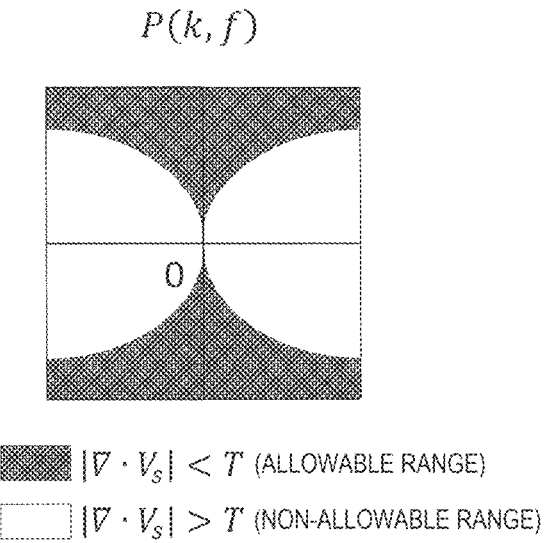
$|\nabla \cdot V_s| < T$ (ALLOWABLE RANGE)
$|\nabla \cdot V_s| > T$ (NON-ALLOWABLE RANGE)

[FIG. 17A]
ALLOWABLE RANGE
DETERMINED BY THRESHOLD
[FIG. 17B]
FREQUENCY DISTRIBUTION
IN k-f SPACE ROTATED BY $\alpha_{tmp}$
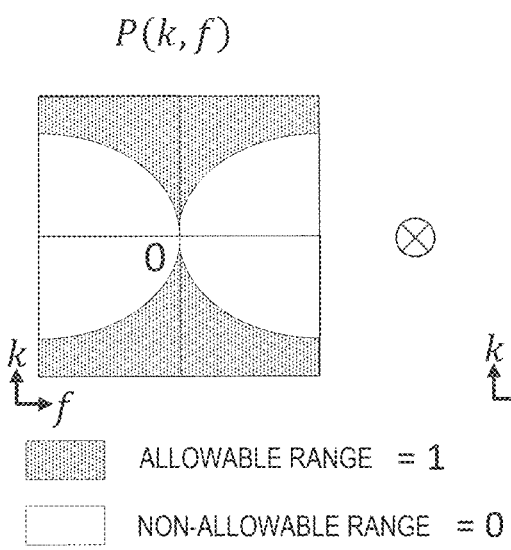
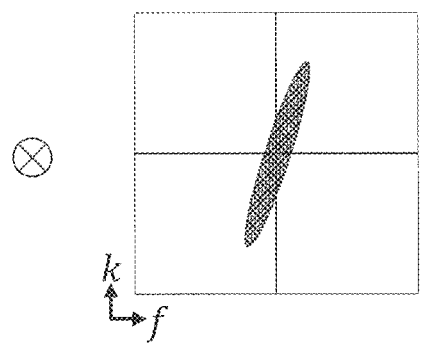

[FIG. 18A]
FILTER PROCESSING OF ROTATED
k-f FREQUENCY DISTRIBUTION
[FIG. 18B]
k-f FREQUENCY
DISTRIBUTION AFTER
FILTER PROCESSING
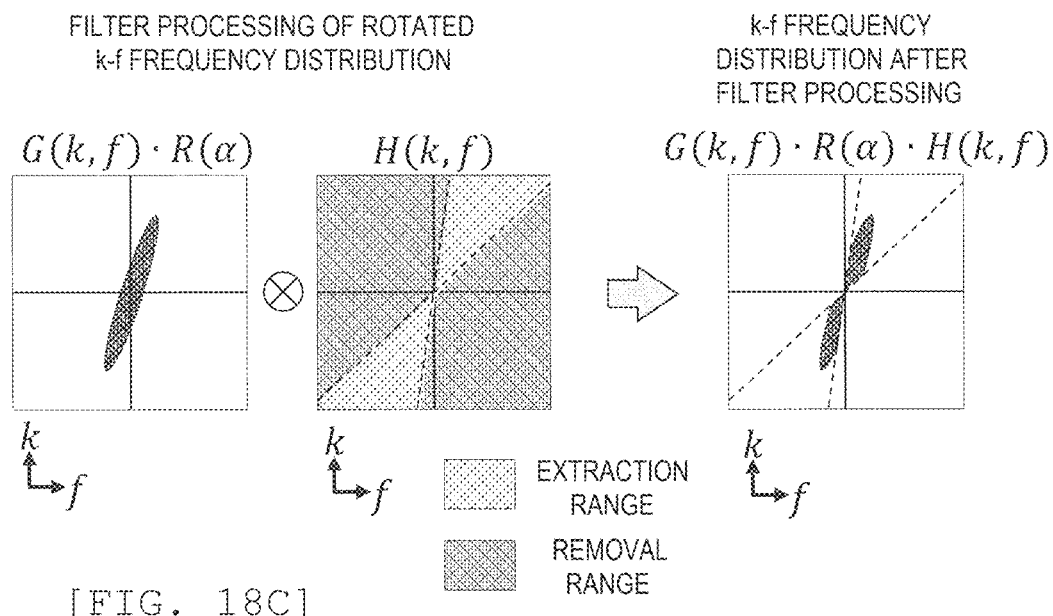
[FIG. 18C]
x-t DISPLACEMENT DISTRIBUTION AFTER FILTER PROCESSING
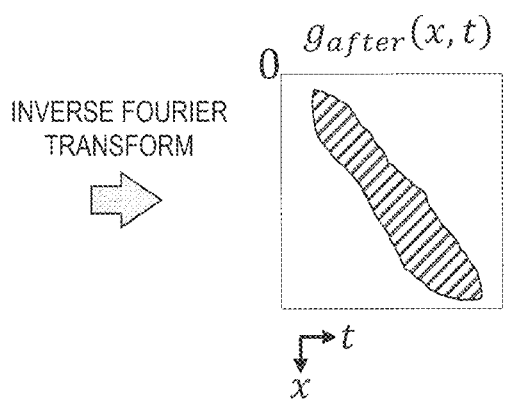

[FIG. 19]
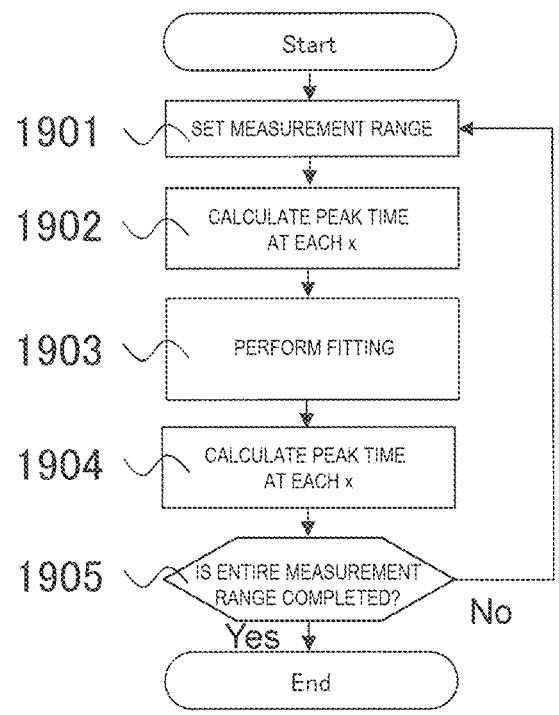

[FIG. 20A]
METHOD FOR DETECTING PEAK TIME IN x-t
DISPLACEMENT DISTRIBUTION AFTER FILTER PROCESSING
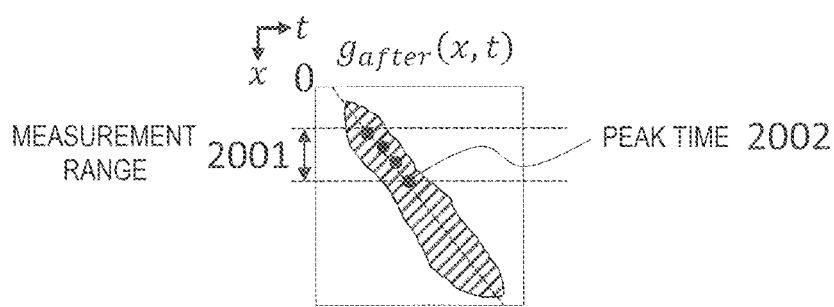
[FIG. 20B]
FITTING EXAMPLE OF PEAK TIME
IN x-t DISPLACEMENT DISTRIBUTION
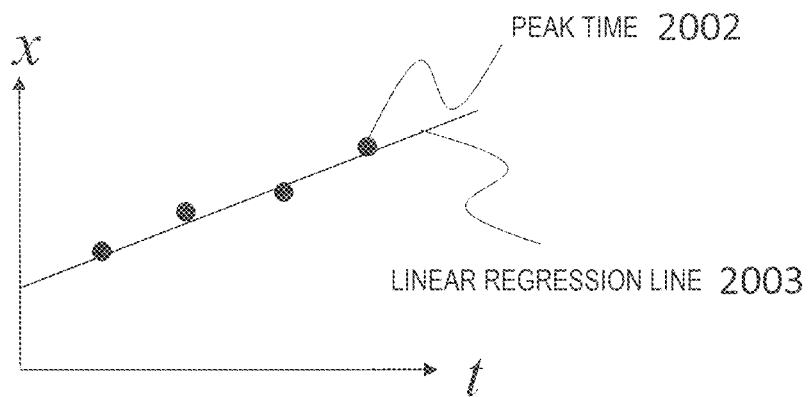

[FIG. 21]
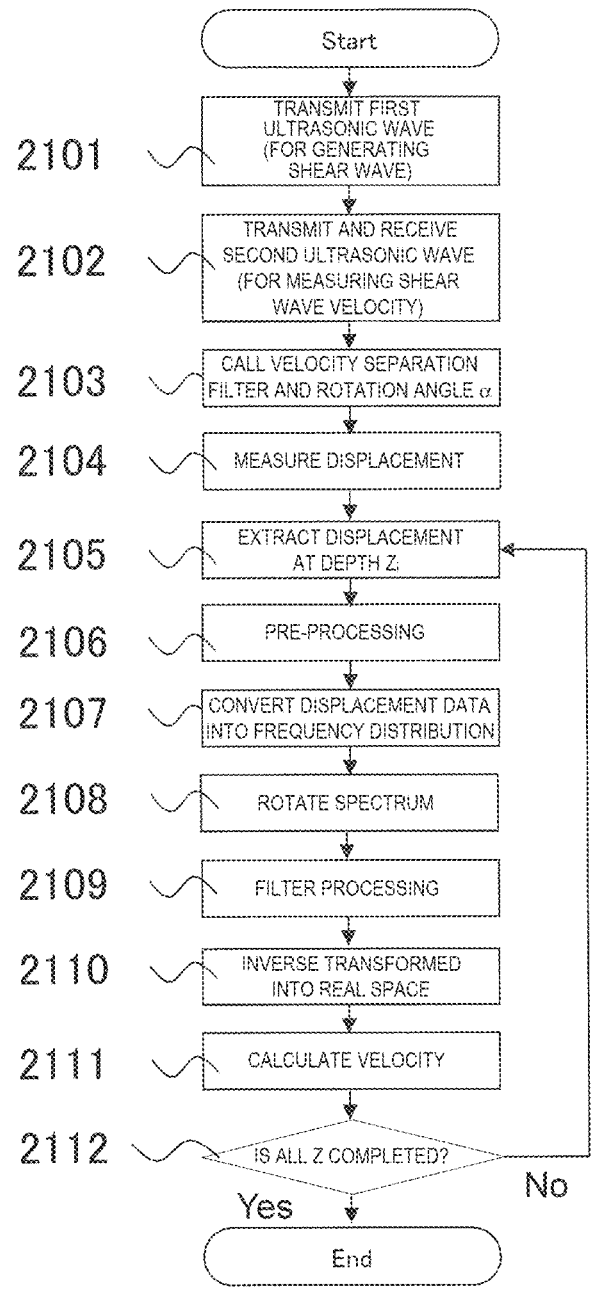

[FIG. 22]
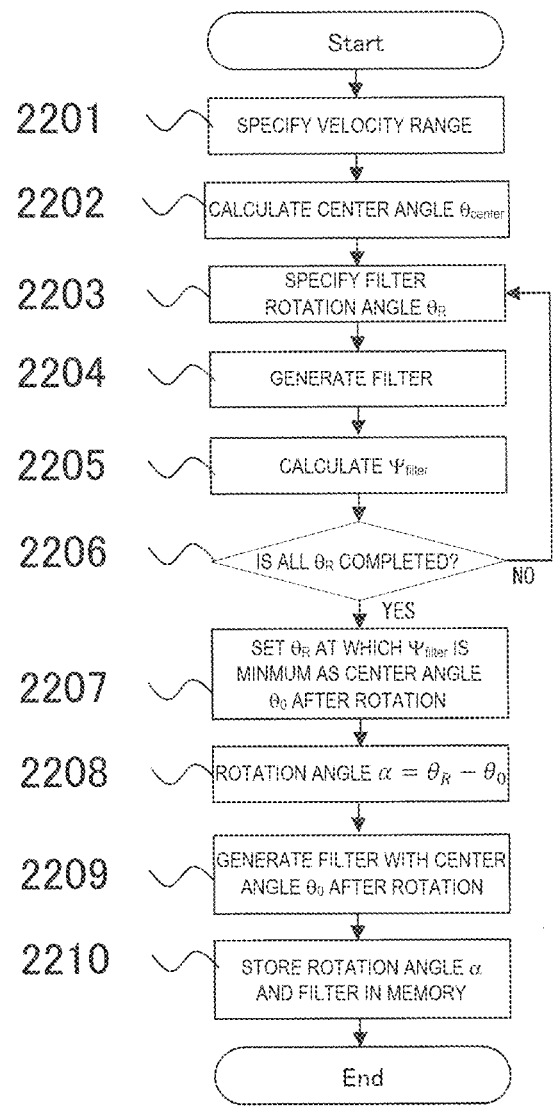

[FIG. 23]
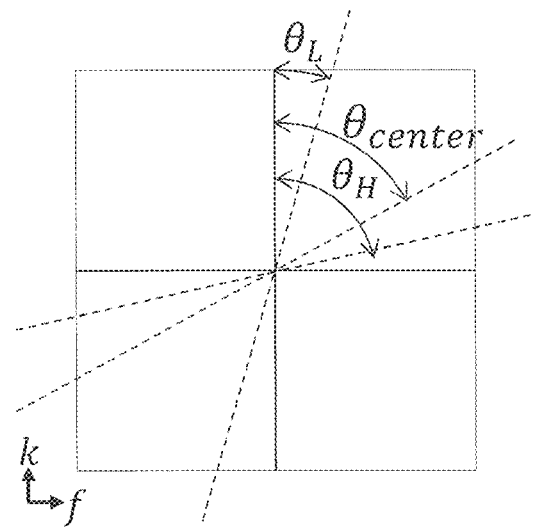
[FIG. 24]
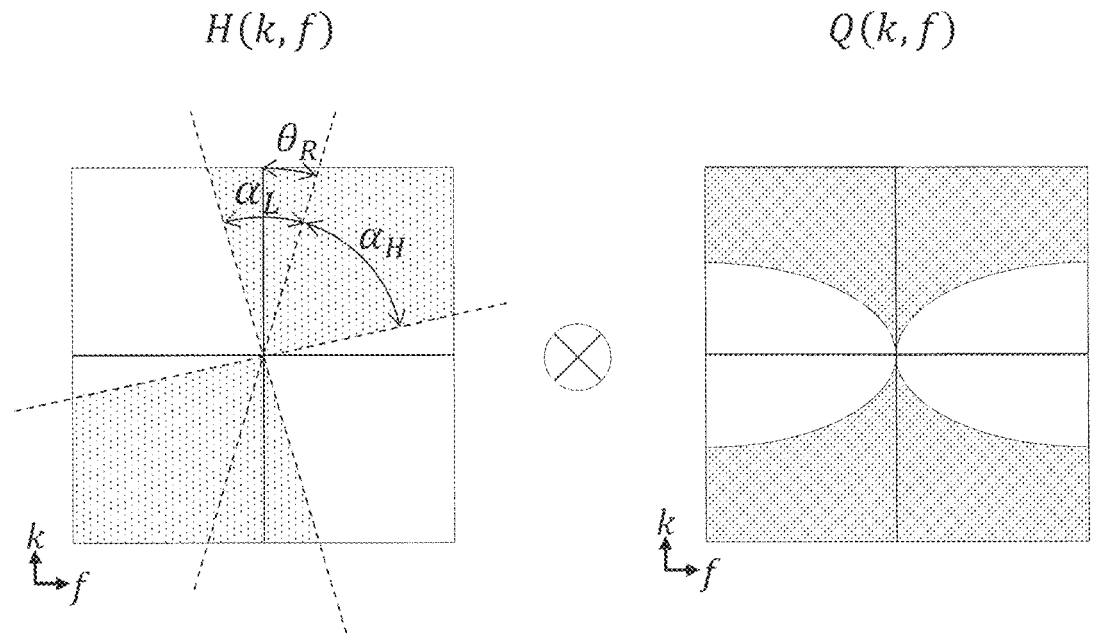

[FIG. 25]
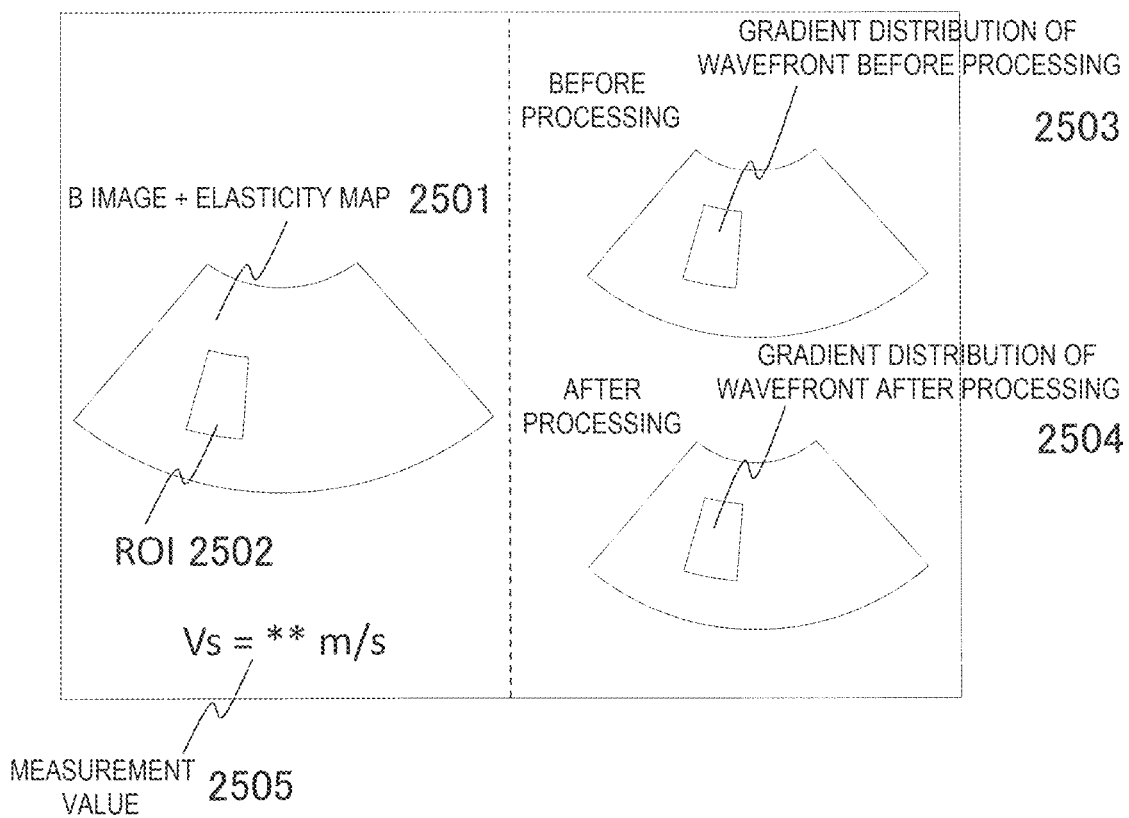

[FIG. 26]
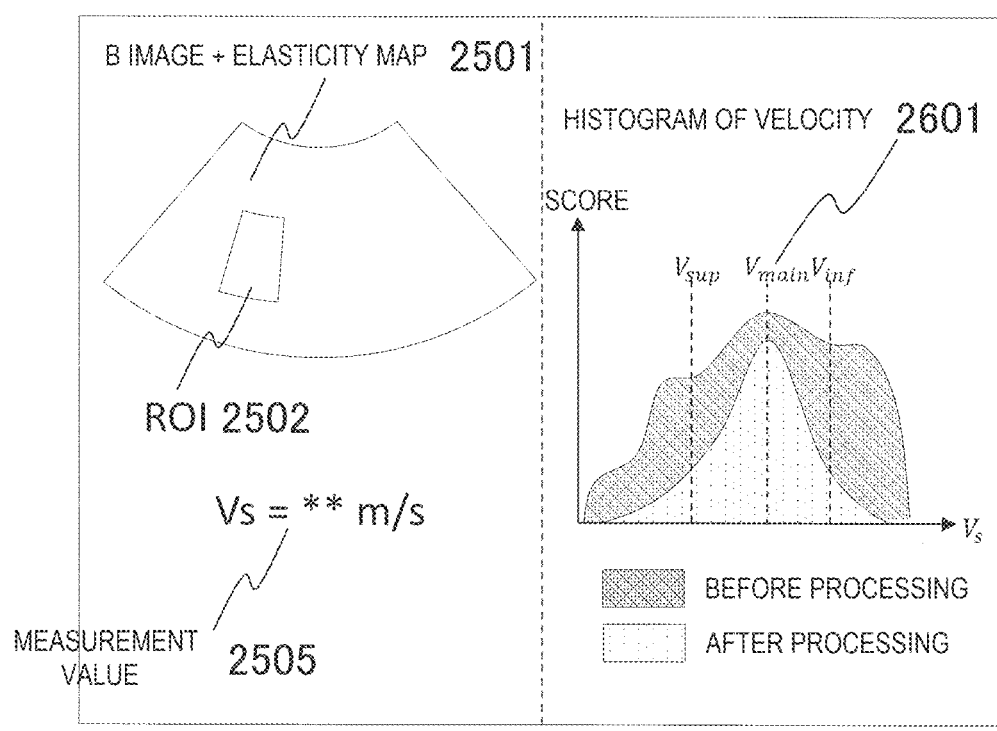

[FIG. 27]
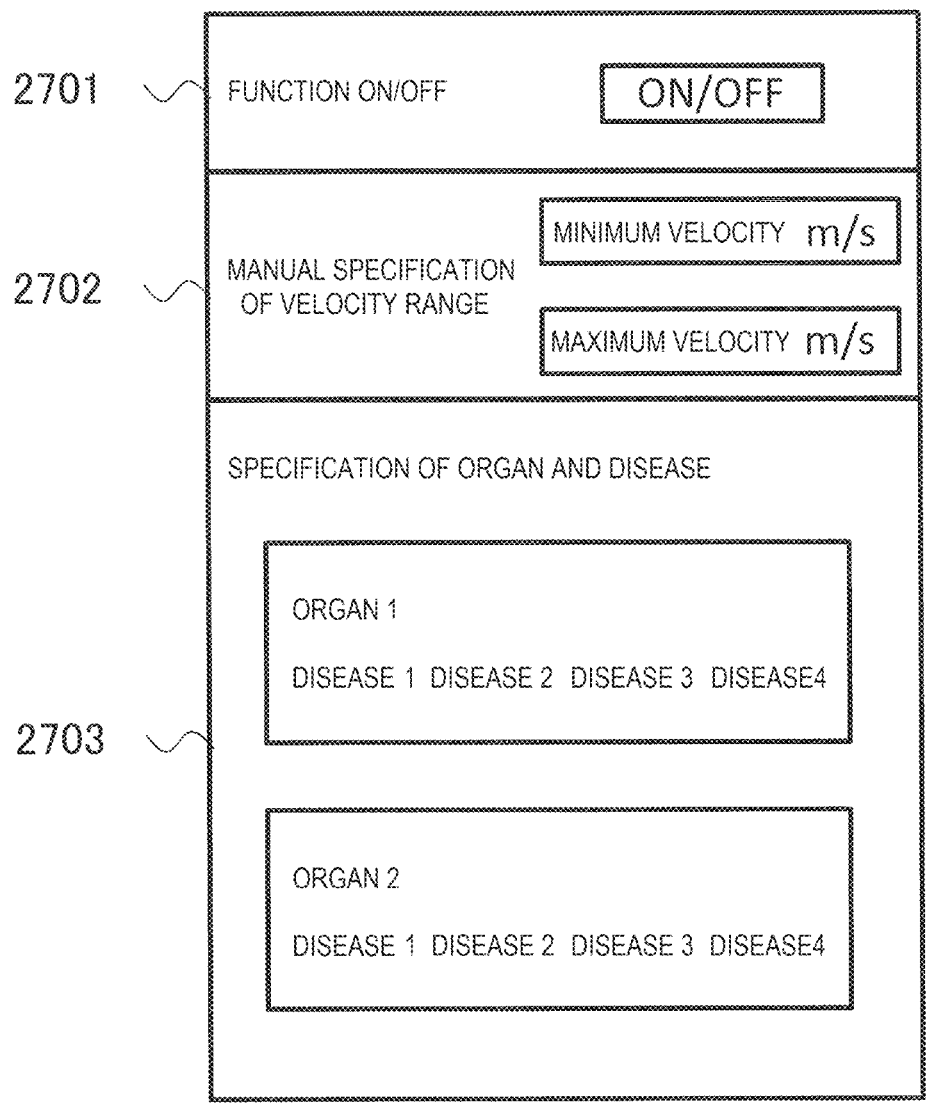

[FIG. 28]

| ORGAN NAME | DISEASE NAME | VELOCITY RANGE |
|---|---|---|
| ORGAN 1 | DISEASE 1 | ☐m/s - ☐m/s |
|  | DISEASE 2 | ☐m/s - ☐m/s |
|  | DISEASE 3 | ☐m/s - ☐m/s |
| ORGAN 2 | DISEASE 1 | ☐m/s - ☐m/s |
|  | DISEASE 2 | ☐m/s - ☐m/s |
|  | DISEASE 3 | ☐m/s - ☐m/s |
| ORGAN 3 | DISEASE 1 | ☐m/s - ☐m/s |
|  | DISEASE 2 | ☐m/s - ☐m/s |
|  | DISEASE 3 | ☐m/s - ☐m/s |

ULTRASONIC DIAGNOSTIC DEVICE, SIGNAL PROCESSING DEVICE, AND PROGRAM

CROSS-REFERENCE TO RELATED APPLICATION

The present application claims priority from Japanese application JP2019-072288, filed on Apr. 4, 2019, the contents of which is hereby incorporated by reference into this application.

TECHNICAL FIELD

The present invention relates to an ultrasonic diagnostic device, and relates to a technique for evaluating properties of a living tissue by generating a shear wave in a subject and measuring a propagation velocity of the shear wave.

BACKGROUND ART

Medical image display devices typified by ultrasonic waves, magnetic resonance imaging (MRI), and X-ray computed tomography (CT) have been widely used as devices that present information in a living body, that cannot be visually confirmed, in a form of values or images. Among the above devices, an ultrasonic imaging device that displays an image using ultrasonic waves has a high temporal resolution as compared to other devices, and has, for example, a performance capable of imaging a heart during pulsation without blurring.

Waves propagating in a living body which is a subject are mainly classified into longitudinal waves and transverse waves. A technique for visualizing a shape of a tissue on which a product of the ultrasonic imaging device is mounted and a technique for measuring a blood flow velocity mainly use information of the longitudinal wave (sound velocity is about 1540 m/s).

In recent years, a technique for evaluating an elastic modulus of a tissue using the transverse wave (hereinafter referred to as a shear wave) propagating in the living body has been attracting attention, and clinical use for chronic liver disease and cancer has been promoted. In this technique, the shear wave is generated inside a tissue to be measured, and an evaluation index representing elasticity such as an elastic modulus is calculated from a propagation velocity. Methods for generating the shear wave are roughly classified into a mechanical method and a radiation pressure method. The mechanical method is a method of generating a shear wave by applying a vibration of about 1 kHz to a body surface by using a vibrator or the like, and requires a driving device as a vibration source. On the other hand, in the radiation pressure method, an acoustic radiation pressure is applied to the living body by using focused ultrasonic waves that allow the ultrasonic waves to be locally concentrated in the tissue, and the shear wave is generated using tissue displacement that occurs instantaneously. In either method, the propagation velocity is calculated by measuring the tissue displacement due to the generated shear wave with the ultrasonic wave. Further, a characteristic value of an elastic modulus and the like representing tissue properties is obtained by calculation from the calculated propagation velocity of the shear wave.

In this way, the method for evaluating the elasticity of the tissue using the shear wave is extremely important in a tumor diagnosis and has a high clinical value because the elasticity can be measured quantitatively. However, it is known that when the elasticity of the tissue is measured using the shear wave, the shear wave is reflected, refracted, diffracted, or attenuated by the tissue structure, thereby the measurement accuracy and the reproducibility are reduced and the diagnostic performance is deteriorated.

For example, Patent Literature 1 discloses a method in which a distribution of wavefront amplitude of a shear wave propagating in an test object is measured, data is subjected to a Fourier transform and filtered in the Fourier space, thereby a main component that is a measurement object of the shear wave is separated from reflection, refraction, and diffraction components, and the main component is extracted.

Specifically, in a technique of Patent Literature 1, wavefront amplitude data of the shear wave propagating at a depth z of the test object is plotted on a two-dimensional plane of azimuth direction-time (x-t plane), and the wavefront amplitude data is converted into an intensity distribution in a two-dimensional plane of a two-dimensional Fourier space (k-f plane) having a spatial frequency k and a time frequency f by performing a two-dimensional Fourier transform on the wavefront amplitude data. Since a shear wave velocity is proportional to an angle θ between a k axis and a straight line connecting a point of the wavefront amplitude data and an origin point in the k-f plane, filter processing for extracting the wavefront amplitude data in a predetermined angle range is performed so as to extract only a velocity component in the vicinity of a main component. The wavefront amplitude data in the k-f plane after the filter processing is converted into a real space (x-t plane) by an inverse Fourier transform, and the velocity is calculated. By performing the processing for all depths z, a shear wave velocity map of the entire x-z plane can be generated.

CITATION LIST

Patent Literature

PTL 1: JP-A-2018-99180

SUMMARY OF INVENTION

Technical Problem

In order to accurately obtain the elastic modulus representing the tissue properties by calculation from the propagation velocity of the shear wave by the above radiation pressure method, it is necessary to accurately calculate the propagation velocity. For example, it is conceivable to assume a propagation direction and provide two or more measurement points in advance, and a time required to pass through the two measurement points is accurately measured, but the shear wave does not always propagate horizontally with respect to a measurement line. Since the shear wave is affected by reflection, refraction, diffraction, attenuation, and the like due to the tissue structure in a body and a physical principle of sound wave propagation, the shear wave includes various frequencies and travel direction components. For this reason, it is difficult to measure the shear wave velocity with high accuracy and reproducibility without being affected by reflected waves and the like.

In the technique described in PTL 1, the main component of the shear wave can be extracted by applying the Fourier transform and performing the filter processing for extracting the wavefront amplitude data in the predetermined angle range in the Fourier space (k-f plane).

However, in a region where the angle θ is large (the shear wave velocity is large), a corresponding relationship between the angle θ, which is formed by the straight line connecting the point of the wavefront amplitude data in the k-f plane and the origin point and the k axis, and the propagation velocity has a characteristic that a corresponding propagation velocity varies greatly depending on a slight angle change, so that it is not easy to accurately extract only the main component with a filter.

An object of the invention is to provide an ultrasonic diagnostic device that can accurately measure a shear wave velocity.

Solution to Problem

In order to achieve the above object, according to the invention, an ultrasonic diagnostic device is provided. The ultrasonic diagnostic device includes: a measurement unit configured to calculate time change data of a displacement of a tissue due to a shear wave generated in an test object, from a reception signal obtained by transmitting an ultrasonic wave to the test object and receiving a reflected wave; an extraction unit configured to extract spectrum data in a predetermined region by converting the time change data of the displacement into spectrum data indicating a displacement distribution in a frequency space having a spatial frequency and a time frequency as two axes, and filtering the spectrum data in the frequency space; and a velocity calculation unit configured to calculate a velocity of the shear wave based on the spectrum data in the predetermined region extracted by the extraction unit. The extraction unit includes a spectrum rotation unit configured to rotate the spectrum data by a predetermined angle in the frequency space, and is configured to extract the spectrum data in the predetermined region by filtering the rotated spectrum data.

Advantageous Effect

According to the invention, the shear wave velocity can be accurately measured.

BRIEF DESCRIPTION OF DRAWINGS

FIG. 1 is a block diagram showing a configuration example of an ultrasonic diagnostic device according to an embodiment of the invention.

FIG. 2 is a flowchart showing an operation of an ultrasonic diagnostic device according to a first embodiment.

FIG. 3 is an explanatory diagram showing a method for transmitting and receiving an ultrasonic wave according to the embodiment.

FIG. 4A is an explanatory diagram showing how a shear wave propagates, FIG. 4B is an explanatory diagram showing time-series information about propagation of the shear wave, and FIG. 4C is an explanatory diagram showing a displacement distribution in an x-t plane at a certain depth $Z_i$.

FIG. 5A is a diagram showing a displacement distribution in the x-t plane at a certain depth, FIG. 5B is a diagram showing a power spectrum in a k-f plane obtained by performing a two-dimensional Fourier transform on FIG. 5A, and FIG. 5C is a diagram showing filter processing performed on FIG. 5B.

FIG. 6A is a diagram showing a contour distribution of a velocity distribution in a first quadrant of a filter, FIG. 6B is a diagram showing a vector distribution of a velocity gradient distribution calculated from the velocity distribution in FIG. 6A, FIG. 6C is a diagram showing a contour distribution of an absolute value of the velocity gradient in FIG. 6B, FIG. 6D is a diagram showing a contour distribution of a velocity distribution of the entire filter in order to clarify a position of the first quadrant on the filter, and FIG. 6E is a diagram showing a velocity range per mesh.

FIG. 7A is a diagram showing a displacement distribution in the x-t plane at a certain depth, FIG. 7B is a diagram showing a power spectrum in the k-f plane obtained by performing a two-dimensional Fourier transform on FIG. 7A, and FIG. 7C is a diagram showing a power spectrum obtained by rotating FIG. 7B by α.

FIG. 8A is a diagram showing a filter that extracts a predetermined angle range. FIG. 8B is a diagram showing a determination method of an extraction radius range of the filter. FIG. 8C is a diagram showing a filter generated based on the extraction angle and the extraction radius which are respectively determined in FIGS. 8A and 8B.

FIG. 9 is a flowchart showing a processing flow of a method for calculating a main component by searching for a peak on an arc.

FIGS. 10A and 10B are diagrams showing an outline of the method for calculating the main component by searching for the peak on the arc.

FIG. 11 is a flowchart showing a processing flow of a method for calculating the main component based on a Radon transform.

FIGS. 12A and 12B are diagrams showing an outline of the method for calculating the main component by the Radon transform.

FIG. 13 is a flowchart showing a processing flow of a method for determining a rotation angle of a power spectrum in the k-f plane based on the distribution of the absolute value of the velocity gradient.

FIGS. 14A and 14B are diagrams showing an outline of the method for determining the rotation angle of the power spectrum in the k-f plane based on the distribution of the absolute value of the velocity gradient.

FIG. 15 is a diagram showing a processing flow of a method for determining the rotation angle of the power spectrum in the k-f plane by threshold processing.

FIGS. 16A and 16B are diagrams showing a method for determining an allowable range based on a threshold in the method for determining the rotation angle of the power spectrum in the k-f plane by the threshold processing.

FIGS. 17A and 17B are diagrams showing an outline of the method for determining the rotation angle of the power spectrum in the k-f plane by the threshold processing.

FIG. 18A is a diagram showing filter processing for the power spectrum in the rotation k-f plane, FIG. 18B is a diagram showing the power spectrum in the rotated k-f plane after the filter processing, FIG. 18C is a diagram showing a displacement distribution in the x-t plane obtained by performing an inverse Fourier transform on FIG. 18B.

FIG. 19 is a diagram showing a processing flow of a method for calculating a shear wave velocity by fitting.

FIGS. 20A and 20B are diagrams showing an outline of the method for calculating the shear wave velocity by the fitting.

FIG. 21 is a flowchart showing an operation of an ultrasonic diagnostic device according to a second embodiment.

FIG. 22 is a flowchart showing a processing flow for generating a rotation angle and a filter of a k-f space distribution and storing the rotation angle and the filter in a memory.

FIG. 23 is a diagram showing a method for obtaining a center angle.

FIG. 24 is a diagram showing a method for obtaining a center angle of the filter.

FIG. 25 is a diagram showing an example of a display screen on a display unit of the ultrasonic diagnostic device, which is an example of a screen in which a B image, and elasticity or shear wave velocity map is displayed, and wavefront gradient distributions before and after the filter processing are displayed.

FIG. 26 is a diagram showing an example of the display screen on the display unit of the ultrasonic diagnostic device, which is an example of a screen in which the B image, and elasticity or shear wave velocity map is displayed, and velocity distributions in ROI before and after the filter processing, the main component, and a velocity range of the filter are displayed.

FIG. 27 is a diagram showing an example of the display screen on the display unit of the ultrasonic diagnostic device, which is an example of the display screen of input screen areas 2701 to 2703 where a user inputs the velocity range.

FIG. 28 is a diagram showing an example of a table stored in the memory of the ultrasonic diagnostic device, which is an example of a table showing a relationship between selectable organs and diseases and velocity ranges suitable for the organs and the diseases.

DESCRIPTION OF EMBODIMENTS

First Embodiment

Hereinafter, embodiments of the invention will be described with reference to drawings.

<Overall Configuration of Ultrasonic Diagnostic Device>

FIG. 1 shows a block diagram of a configuration example of an ultrasonic diagnostic device according to an embodiment. The ultrasonic diagnostic device of the present embodiment includes a transmission and reception control unit 20 and a control unit (signal processing device) 30. Further, a probe 10, an external input device 13, and a display unit 16 are connected to the ultrasonic diagnostic device.

The transmission and reception control unit 20 includes a transmission beamformer 21 that generates a transmission signal to be transferred to each vibrator constituting the probe 10, and a reception beamformer 22 that generates a reception signal for a predetermined point in an test object 100 based on output of each vibrator of the probe 10. Further, the control unit 30 includes a measurement unit 31, a filter generation unit 32, a main component extraction unit 33, a velocity calculation unit 34, and an image generation unit 35.

In the probe 10, vibrators (elements) serving as sound sources are regularly arranged. For each of the elements, the transmission beamformer 21 outputs a transmission signal delayed by a predetermined delay time. The vibrator is vibrated by the transmission signal to form a desired ultrasonic beam. The transmitted ultrasonic beam is, for example, reflected inside the test object and returned to the probe 10. The probe 10 converts the returned ultrasonic wave into a signal and sends the signal to the reception beamformer 22. The reception beamformer 22 generates a reception signal (radio frequency (RF) signal) by phasing and adding output signals of the vibrator at a plurality of points on a reception scanning line.

The measurement unit 31 measures a displacement of a tissue inside the test object 100 in time series using the RF signal.

The filter generation unit 32 generates a filter used in the main component extraction unit 33 based on a signal sent from the transmission and reception control unit 20 to the control unit 30, a parameter used in the transmission and reception control unit 20, and information received from the external input device 13. The filter generation unit 32 includes a spectrum rotation unit 37 for improving the accuracy of extraction of a main component of a shear wave.

The main component extraction unit extracts a main component 403 of the shear wave by applying the filter to shear wave data.

The velocity calculation unit 34 calculates a shear wave velocity from the main component of the shear wave obtained by the main component extraction unit 33.

The image generation unit 35 generates image data of the shear wave velocity obtained by the velocity calculation unit 34 or image data of an elastic modulus obtained by converting the shear wave velocity, and sends the image data to the display unit 16.

The measurement unit 31, the filter generation unit 32, the main component extraction unit 33, the velocity calculation unit 34, and the image generation unit 35 of the control unit 30 can be implemented by software, and a part of or all the control unit 30 can also be implemented by hardware. When the control unit 30 is implemented by the software, the control unit 30 is configured with a processor such as a central processing unit (CPU) or a graphics processing unit (GPU), and realizes functions of the measurement unit 31, the filter generation unit 32, the main component extraction unit 33, the velocity calculation unit 34, and the image generation unit 35 by reading and executing programs stored in advance in the control unit 30. Further, when the control unit 30 is implemented by software, a circuit may be designed using a custom IC such as an application specific integrated circuit (ASIC) or a programmable IC such as a field-programmable gate array (FPGA) so as to realize at least operations of the measurement unit 31, the filter generation unit 32, the main component extraction unit 33, the velocity calculation unit 34, and the image generation unit 35.

<Operation of Each Unit of Ultrasonic Diagnostic Device>

Hereinafter, the operation of each unit described above will be specifically described with reference to FIGS. 2 to 5. Here, a case where the control unit 30 is implemented by the software will be described as an example. FIG. 2 is a flowchart showing operations of the entire device. FIG. 3 is an explanatory diagram schematically showing positions and transmission directions of ultrasonic waves transmitted from and received by the probe 10. FIG. 4A is a diagram showing a displacement distribution and a propagation direction of the tissue due to the shear wave in an x-z plane, FIG. 4B is a diagram showing that the displacement distribution of the tissue due to the shear wave is obtained in time series, and FIG. 4C is a diagram showing a displacement distribution of the tissue due to the shear wave of FIG. 4B in an x-t plane at a certain depth $Z_i$ of the test object. FIG. 5A shows an angle formed by a direction in which an intensity of the displacement distribution in the x-t plane of FIG. 4C is large and a t direction, FIG. 5B shows a displacement distribution (power spectrum) in a spatial frequency-time frequency (k-f) plane obtained by the displacement distribution in the x-t plane being subjected to a two-dimensional Fourier transform, and FIG. 5C shows an example of a filter that extracts displacement data in a specific range in the power spectrum in the (k-f) plane.

((Step 201))

First, in step 201, the control unit 30 instructs the transmission and reception control unit 20 to transmit, from the probe 10, a first ultrasonic wave 301 having an intensity capable of generating a shear wave in the test object 100. Since an acoustic radiation pressure is generated near a focal point of the first ultrasonic wave 301 and the pressure is locally applied to the test object 100 which is irradiated with the first ultrasonic wave 301, a shear wave is generated around the focal point and propagates radially. Accordingly, the shear wave can be propagated into an ROI 300 which is set in the test object 100.

Specifically, the control unit 30 instructs the transmission and reception control unit 20 to determine a position of the region of interest (ROI) 300 in the test object 100 shown in FIG. 3. The transmission and reception control unit 20 causes the transmission beamformer 21 to generate a transmission signal. The generated transmission signal is output to each vibrator constituting the probe 10. Accordingly, the first ultrasonic wave having a predetermined acoustic intensity and focused on a focal point at a predetermined depth is transmitted from the probe 10 to the ROI 300 or a predetermined position in the vicinity thereof. The acoustic radiation pressure is applied near the focal point of the first ultrasonic wave 301 in the test object 100, and when transmission of the first ultrasonic wave 301 is stopped, a pressure load is eliminated and a restoring force acts, so that the shear wave is generated in the test object 100. The shear wave propagates radially with a position irradiated with the first ultrasonic wave 301 as a base point. In FIG. 3, the first ultrasonic wave 301 is transmitted such that a shear wave 303 propagating in a right direction from the focal point of the first ultrasonic wave 301 passes through the ROI 300.

Assuming that the test object 100 is homogeneous and spreads infinitely, as shown in FIG. 3, the shear wave generated by the radiation pressure propagates in the test object 100 in a direction perpendicular to a direction (depth direction) 401 in which the radiation pressure is applied. However, since an actual shear wave is, for example, refracted, reflected, and diffracted due to an inhomogeneous tissue structure in a living body and physical properties of ultrasonic wave propagation, the shear wave propagates in various directions as shown in FIG. 4A. As a result, the shear wave has components such as a refracted, reflected, diffracted wave 402 in addition to the main component and these components overlap, so that the shear wave has various frequency components and velocity components. Therefore, in the embodiment, in steps 210 and 211 to be described later, the filter generation unit 33 generates the filter for extracting the main component 403 that is a true measurement object from the various components of the shear wave. The main component extraction unit 33 calculates a velocity of the main component 403 from the shear wave data after filter processing. The operations of steps 210 and 211 will be described in detail later.

((Step 202))

Next, in step 202, the control unit 30 instructs the transmission and reception control unit 20, as shown in FIG. 3, to transmit a second ultrasonic wave 302 for measuring the shear wave velocity from the probe 10 to the ROI 300 and receive a reflected wave and the like. The second ultrasonic wave 302 is sequentially transmitted toward measurement points 304 set at, for example, equal intervals in a direction (for example, an x direction) in which the shear wave in the ROI 300 propagates. Specifically, the transmission and reception control unit 20 causes the transmission beamformer 21 to generate a transmission signal, and the transmission signal is output to each vibrator of the probe 10. Accordingly, the second ultrasonic wave 302 is sequentially transmitted from the probe 10 to the plurality of measurement points 304 at predetermined timings.

Each of the second ultrasonic waves 302 is, for example, reflected at the measurement point 304, returned to the probe 10, and received by the vibrators of the probe 10. The transmission and reception control unit 20 sets a plurality of reception scanning lines respectively passing through the plurality of measurement points 304 of the second ultrasonic wave 302 and extending in a depth direction (a z direction). The reception beamformer 22 performs reception beamforming processing such as phasing addition on the reception signals of each vibrator, and thereby obtaining a phased reception signal that focuses on each of a plurality of points (reception focal points) at a depth z set on the reception scanning line. Accordingly, the RF signal in which the phased reception signals are connected in a reception scanning line direction is generated.

The transmission and reception control unit 20 repeats transmission of the second ultrasonic wave 302 and reception of the reflected wave and the like with predetermined time intervals, and generates RF signals for each of the plurality of reception scanning lines for each elapsed time.

((Step 203))

In step 203, the measurement unit 31 of the control unit 30 measures a displacement (amplitude of the shear wave) for each of the plurality of reception focal points in the z direction (the depth direction) on the reception scanning line, based on the RF signal. Specifically, the displacement of the tissue is obtained for each of the reception focal points including the plurality of measurement points 304 by cross-correlation calculation between the RF signals obtained in time series for the same reception scanning line. Accordingly, the measurement unit 31 can obtain the distribution of the displacement (the amplitude) of the shear wave in a z-x plane in time series (see FIG. 4B).

((Step 204))

In step 204, the measuring unit 31 obtains time changes of the displacement (the displacement distribution in the x-t plane) at the certain depth $Z_i$ as shown in FIG. 4C from time-series information of the distribution of the displacement (the amplitude) of the shear wave in the z-x plane as shown in FIG. 4B.

((Step 205))

In step 205, the filter generation unit 32 removes a noise that is easily separated and is included in the displacement distribution in the x-t plane of FIG. 4C. For example, since a noise due to a movement of a patient or a shaking of a hand of an operator has a very low frequency compared to an ultrasonic signal, the filter generation unit 32 can easily remove the noise by a known noise removal method. Further, the filter generation unit 32 can also easily remove a noise that appears in the displacement distribution in the x-t plane regularly and periodically, such as a system noise of a device, by a known noise removal method.

((Step 206))

In step 206, as shown in FIGS. 5(a) and 5(b), the filter generation unit 32 performs a two-dimensional Fourier transform on the displacement distribution in the x-t plane, thereby converting the displacement distribution in the x-t plane into a displacement distribution (hereinafter referred to as the power spectrum) in a plane, that is, the (k-f) plane having the spatial frequency k and the time frequency f as two axes.

As shown in FIG. 5A, in the displacement distribution in the x-t plane, a shear wave velocity $V_s$ in a section $\Delta x$ is represented by an angle $\theta$ formed by an axial direction 51 where the displacement of the power spectrum is large and a time t axis. The shear wave velocity $V_s$ is represented by the following Equation (1).

$$V_s = \frac{x}{t} = \tan\theta \qquad \text{[Equation 1]}$$

On the other hand, in the power spectrum in a frequency space k-f plane, as shown in FIG. 5B, the velocity $V_s$ is represented by the angle $\theta$ formed by the axial direction 51 (a direction of the main component 403) where the displacement (amplitude) is large and a spatial frequency k axis. The shear wave velocity $V_s$ is represented by the following Equation (2).

$$V_s = \frac{f}{k} = \tan\theta \qquad \text{[Equation 2]}$$

As is apparent from Equations (1) and (2), the shear wave velocity in the displacement distribution in the x-t plane and in the power spectrum in the k-f plane can be represented using the common angle $\theta$.

((Steps 207 to 213))

In steps 207 to 210, as shown in FIG. 5C, the filter generation unit 32 generates a filter 502 that extracts a component in a predetermined angle range around the axial direction 51 (the direction of the main component 403) where the displacement of the power spectrum in the k-f plane is large. In step 211, the main component extraction unit 33 extracts the main component 403 and components around the main component 403 and removes other components by applying the filter 502 to the power spectrum in the k-f plane.

(Description of Extraction Accuracy of Main Component by Filter 502)

Here, the extraction accuracy of the main component 403 of the filter 502 generated by the filter generation unit 32 will be described.

As can be seen from the above Equation (2), in the power spectrum in the k-f plane, the angle $\theta$ formed by the spatial frequency k axis and the axial direction (the direction of the main component 403) 51 where the displacement is large and the velocity $V_s$ is not in a linear relationship. Specifically, a change in the angle $\theta$ decreases as the velocity $V_s$ increases (the angle $\theta$ increases). Therefore, a constant velocity line 601 in the k-f plane is as shown in FIGS. 6(*a*) and 6(*d*), and in a low velocity region where the angle $\theta$ formed by the main component direction 51 and the spatial frequency k axis is small, the constant velocity line 601 is sparse, but in a high velocity region where the angle $\theta$ formed by the main component direction 51 and the spatial frequency k axis is large (close to 90 degrees), the constant velocity line 601 is dense. FIG. 6A shows the constant velocity line 601 only in a first quadrant of the power spectrum in the frequency space k-f of FIG. 5B, and FIG. 6D shows the constant velocity line 601 in four quadrants.

A gradient $\nabla \cdot V_s$ of a velocity distribution is represented by Equation (3) and can be illustrated as shown in, for example, FIG. 6B. Further, an absolute value of the gradient of the velocity distribution is represented as shown in Equation (4) and can be illustrated as shown in FIG. 6C.

$$\nabla \cdot V_s = \frac{f}{k} = \frac{\partial}{\partial k} \cdot \frac{f}{k} + \frac{\partial}{\partial f} \cdot \frac{f}{k} \qquad \text{[Equation 3]}$$

$$|\nabla \cdot V_s| \qquad \text{[Equation 4]}$$

As described above, the filter generation unit 32 can extract the main component 403 and the components around the main component 403 by extracting a specific angle component around the main component direction 51 with the filter, as shown in FIG. 5C. At this time, as shown in FIGS. 6A and 6D, the constant velocity line 601 in the frequency space k-f plane becomes denser as an angle from the spatial frequency k axis (that is, velocity) increases. On the other hand, the power spectrum (displacement distribution) in the frequency space k-f plane is a discrete signal, the frequency space k-f plane is divided into meshes (pixels) having a uniform size, and a displacement value is assigned to each of the meshes. For this reason, a velocity resolution of one mesh differs depending on a position of the mesh. The mesh will be specifically described with reference to FIG. 6E.

FIG. 6E shows a mesh 604 located near the spatial frequency k axis and a mesh 605 located near the time frequency f axis among the meshes constituting the k-f plane. Sizes of the mesh 604 and the mesh 605 are the same. In FIG. 6E, the sizes of the meshes 604 and 605 are shown larger than actual sizes for easy understanding. The mesh 604 is located in a region where the velocity gradient is small, whereas the mesh 605 is located in a region where the velocity gradient is large, so that the velocity resolution of the mesh 605 is lower than the velocity resolution of the mesh 604. That is, when a filter for extracting the mesh 604 is generated, a desired velocity can be extracted with a high velocity resolution, but when a filter for selecting the mesh 605 is generated, because the mesh 605 is in a portion where the velocity gradient is large, a wide range of velocities are extracted and the velocity resolution is reduced.

Therefore, in the present embodiment, the filter generation unit 32 includes the spectrum rotation unit 37 as shown in FIG. 1, and the spectrum rotation unit 37 rotates the power spectrum in the k-f plane with respect to an origin point of the k-f plane. Accordingly, the spectrum rotation unit 37 rotates the power spectrum (spectrum data), thereby moving spectrum data (data in the main component direction 51) in a predetermined region to be extracted to a region where a velocity resolution in the frequency space k-f plane is high. Specifically, the main component direction 51 of the power spectrum is moved to a low velocity region where the angle $\theta$ formed with respect to the spatial frequency k axis is small and the velocity resolution is high.

(Steps 207 to 209)

Specifically, insteps 207 to 209, the spectrum rotation unit 37 rotates the power spectrum (FIG. 7B) 501 in the k-f plane which is obtained by the displacement distribution in the x-t plane in FIG. 7A being subjected to the two-dimensional Fourier transform, by an angle $\alpha$ counterclockwise around the origin point of the k-f plane. Accordingly, displacement data in the main component direction 51 existing in a region where the velocity resolution is low (a region where the velocity is large) in the k-f plane can be moved to a region where the velocity resolution is high (a region where the velocity is small) as shown in FIG. 7C. Details of steps 207 to 209 will be described later.

(Step 210)

In step 210, the filter generation unit 32 generates a filter that extracts a predetermined angle range centered on the main component direction 51 of a power spectrum 701 after a rotational movement, as shown in FIG. 8A.

(Step 211)

The main component extraction unit 33 uses the filter 502 generated by the filter generation unit 32 to perform the filter processing on the power spectrum in the k-f plane, and extracts displacement data of the main component 403 and the components around the main component 403.

(Step 212 to 213)

The velocity calculation unit 34 calculates a velocity from the displacement data of the main component 403 and the components around the main component 403 extracted in step 211. At this time, considering that the axial direction of the main component 403 is rotated by the angle α in step 208, the velocity corresponding to a rotation angle, that is the angle α, is removed, and the velocity of the displacement data of the main component 403 is calculated. Accordingly, since velocity extraction can be performed with a high resolution, the measurement accuracy of the shear wave can be improved.

((Step 214))

The control unit 30 repeats the processing in steps 204 to 213 until the velocity is calculated for all the depths Z (step 214).

<Details of Steps 207 to 209>

Detailed processing in the above steps 207 to 209 will be described.

(Details of Step 207)

In step 207, the spectrum rotation unit 37 obtains the main component direction 51 in the power spectrum 501, and obtains an angle $\theta_{main}$ between the obtained main component direction and the k axis, as shown in FIG. 7B.

A specific example of the processing in step 207 will be described using a processing flow (steps 801 to 804) in FIG. 9 and an explanatory diagram in FIGS. 10A AND 10B.

First, in step 801 in FIG. 9, in a range (the first quadrant) where the angle θ formed with respect to the k axis in the k-f plane is 0 to π/2, the spectrum rotation unit 37 sets an arc $c_1$ having a radius $r_1$, and searches for displacement data having a peak value (maximum value) 901 among the displacement data on the arc $c_i$, as shown in FIG. 10A.

Next, in step 802 in FIG. 9, the spectrum rotation unit 37 calculates an angle $\theta_i$ formed between a line segment, which connects a position of the displacement data of the peak value 901 obtained in step 801 and the origin point, and the k axis.

The spectrum rotation unit 37 repeats the above steps 801 and 802 before the searched radius $r_i$ reaches a predetermined maximum value $r_{max}$ (step 803). The maximum value $r_{max}$ may be automatically determined at every measurement, such as half a length of a diagonal line of the k-f space, or a value may be determined in advance, and the determined value may be stored in a memory and called at the time of measurement.

In step 803 in FIG. 9, if the searched radius reaches the maximum value $r_{max}$, the spectrum rotation unit 37 proceeds to step 804, and calculates a representative value such as a median value or an average value of the angle $\theta_i$ group calculated in step 802, and sets the value as the angle $\theta_{main}$ of the main component 403. FIG. 10B shows a positional relationship between positions of a plurality of the searched peak values 901 and the angle $\theta_{main}$ of the main component 403.

Further, as another method, the angle $\theta_{main}$ of the main component 403 can also be obtained by, for example, a processing flow (steps 1001 to 1003) as shown in FIG. 11. FIGS. 12A and 12b are explanatory diagrams corresponding to the flow of FIG. 11.

In the method, first, in step 1001, a Radon transform is performed on the displacement distribution in the x-t plane in FIG. 12A. Accordingly, for each angle θ in the x-t plane, an integrated value obtained by projecting (integrating) displacement data which is on the angle θ onto a projection plane s is calculated in a θ-s plane. In the θ-s plane, an angle at which the integrated value is the largest is set as the angle $\theta_{main}$ of the main component 403.

(Details of Steps 208 and 209)

Next, step 208 will be described. In step 208, the spectrum rotation unit 37 obtains the rotation angle α of the power spectrum shown in FIG. 7C. The rotation angle α is calculated by, for example, a processing flow as shown in FIG. 13. FIGS. 14A and 14B are explanatory diagrams corresponding to the processing flow of FIG. 13.

First, in steps 1201 to 1203 in FIG. 13, the spectrum rotation unit 37 calculates the velocity distribution of the power spectrum in the k-f plane (step 1201), calculates the velocity gradient $\nabla \cdot V_s$ in the power spectrum in the k-f plane (step 1202), and calculates the absolute value $|\nabla \cdot V_s|$ (step 1203), as shown in FIGS. 6(a) to 6(c).

Next, in step 1204, the spectrum rotation unit 37 rotates the power spectrum G(k, f) in the k-f plane before rotation by an angle $\alpha_{tmp}$ by using a rotation matrix $R(\alpha_{tmp})$ and calculation of Equation (5), and then multiplies the absolute value $|\nabla \cdot V_s|$ of the velocity gradient as in Equation (6) to calculate a cost function $\Psi_{grad}$ (step 1205).

$$G(k,f) \cdot R(\alpha_{tmp}) \quad \text{[Equation 5]}$$

$$\Psi_{grad} = G(k,f) \cdot R(\alpha_{tmp}) \cdot |\nabla \cdot V_s| \quad \text{[Equation 6]}$$

If a larger power (displacement data) exists in a portion where the absolute value of the velocity gradient is small, the velocity can be extracted with a higher resolution. Therefore, in step 1206 in FIG. 13, the spectrum rotation unit 37 searches for the angle $\alpha_{tmp}$, at which the cost function $\Psi_{grad}$ is minimum, within a range of 0<angle $\alpha_{tmp}$<π/2. The obtained angle $\alpha_{tmp}$ is determined as the rotation angle α used in step 209.

Further, the spectrum rotation unit 37 may determine the rotation angle α by another method shown in a flow of FIG. 15. First, in steps 1401 to 1403 in FIG. 15, the spectrum rotation unit 37 calculates the distribution of the absolute value $|\nabla \cdot V_s|$ of the velocity gradient in the power spectrum in the k-f plane, as in steps 1201 to 1203 (FIG. 16A).

Next, in step 1404, the spectrum rotation unit 37 performs threshold processing on the calculated absolute value $|\nabla \cdot V_s|$ of the velocity gradient with a predetermined threshold T, and sets a range in which the absolute value $|\nabla \cdot V_s|$ of the velocity gradient is equal to or less than the threshold as an allowable range (FIG. 16B). Accordingly, the spectrum rotation unit 37 generates a table P(k, f) in which a value of the mesh in a region of the allowable range is set to 1 (FIG. 17A).

The threshold T may be automatically determined for each measurement, or a threshold stored in advance in the memory may be called. As an automatic determination method of the threshold, for example, there is a method in which a certain ratio with respect to the maximum absolute value of the velocity gradient is used as the threshold.

Next, in steps 1405 and 1406, the spectrum rotation unit 37 rotates the power spectrum G(k, f) in the k-f plane before rotation by the angle $\alpha_{tmp}$ by using the rotation matrix $R(\alpha_{tmp})$ and the calculation of Equation (5), and then multiplies the table P(k, f) as in Equation (7) to calculate a cost function $\Psi_{th}$.

$$\Psi_{th}=G(k,f)\cdot R(\alpha_{tmp})\cdot P(k,f) \quad \text{[Equation 7]}$$

If the larger power (displacement data) exists in the allowable range, the velocity can be extracted with a higher resolution. Therefore, in steps 1407 and 1408 in FIG. 15, the spectrum rotation unit 37 searches for the angle $\alpha_{tmp}$, at which the cost function $\Psi_{th}$ is maximum, within the range of $0<\text{angle } \alpha_{tmp}<\pi/2$. The obtained angle $\alpha_{tmp}$ is determined as the rotation angle $\alpha$ used in step 209.

In step 209, the spectrum rotation unit 37 rotates the power spectrum by the rotation angle $\alpha$ obtained in step 208.

(Details of Step 210)

Details of step 210 will be described. In step 210, the filter generation unit 32 generates a velocity separation filter 502. FIGS. 8A to 8C are diagrams showing a method for generating a velocity separation filter. FIG. 8A shows a method for determining an extraction angle range of the velocity separation filter, FIG. 8B shows a method for determining an extraction radius of the velocity separation filter, and FIG. 8C shows a generated filter. In FIG. 8A, $\theta_0$ is an angle obtained by rotating the angle $\theta_{main}$ of the main component by $\alpha$. $\theta_{sup}$ and $\theta_{inf}$, which are angle ranges corresponding to a velocity range to be extracted, are determined by centering on the angle $\theta_0$. Angle differences (angle widths) between $\theta_{sup}$ and $\theta_{inf}$ with respect to $\theta_0$ may be automatically determined for each measurement, or angle differences stored in advance in the memory may be called and used. Next, the filter generation unit 32 determines a radius range to be extracted as shown in FIG. 8B. Since the processing is equivalent to applying a bandpass filter to the entire displacement distribution in the x-t plane, the processing is effective when there are unnecessary components on the power spectrum in the k-f plane that have a clear frequency-dependent characteristic and that cannot be removed only by specifying the extraction angle range. Accordingly, as shown in FIG. 8C, a filter is generated taking into account both conditions of FIGS. 8A and 8b.

After the filter generation unit 32 generates a filter in step 210, in step 211, the main component extraction unit 33 performs the filter processing on the displacement data of the power spectrum in the k-f plane (see FIG. 8A), and extracts the main component 403 and the components around the main component 403 (FIG. 8B).

In step 212, the velocity calculation unit 34 converts the power spectrum in the k-f plane into the displacement distribution in the x-t plane by inverse Fourier transform processing (see FIG. 8C).

When processing in steps 211 and 212 is formulated, the displacement distribution in the x-t plane before the filter processing is defined as $g_{before}(x, t)$, the displacement distribution obtained by converting the above displacement distribution in the x-t plane into the power spectrum in the k-f plane by the two-dimensional Fourier transform is defined as G(k, f), the rotation matrix is defined as R(a), the filter is defined as H(k, f), and the displacement distribution in the x-t plane after the filter processing is defined as $g_{after}(x, t)$, then $g_{before}(x, t)$ and $g_{after}(x, t)$ are in a relationship of Equations (8) and (9).

$$G(k,f)=\mathcal{F}(g_{before}(x,t)) \quad \text{[Equation 8]}$$

$$g_{after}(x,t)=\mathcal{F}^{-1}(G(k,f)\cdot R(\alpha)\cdot H(k,f)), \quad \text{[Equation 9]}$$

wherein F and $F^{-1}$ represents the Fourier transform and the inverse Fourier transform.

<Details of Step 213>

Details of step 213 will be described. In step 213, the velocity calculation unit 34 calculates a velocity. FIG. 19 shows a processing flow for calculating the velocity, and FIGS. 20A and 20B are explanatory diagrams thereof.

First, in step 1901 in FIG. 19, the velocity calculation unit 34 sets a measurement range 2001 for an x axis in the displacement distribution in the x-t plane.

In step 1902, the velocity calculation unit 34 obtains a time t (peak time 2002), at which the displacement of the displacement distribution in the x-t plane has a peak value, at each point on the x axis in the set measurement range (see FIG. 20A).

Next, in step 1903, the velocity calculation unit 34 performs fitting on a plurality of the peak times 2002 calculated in the measurement range 2001 as shown in FIG. 20B. A fitting method includes, for example, linear regression by a least square method and weighted linear regression by an M estimation. The velocity calculation unit 34 can obtain the velocity by obtaining a slope of a straight line when the linear regression is performed.

At this time, the velocity before the rotation can be obtained by subtracting an angle corresponding to the angle $\alpha$ rotated in step 209 from the slope.

The velocity can be obtained for each measurement range by performing steps 1901 to 1904 by moving the measurement range with respect to all x.

(Step 214)

In step 214, the processing from step 204 to step 213 is performed for all z. Therefore, a shear wave velocity map in the x-z plane can be generated. The shear wave velocity map may be displayed on the display unit 16 as it is, or may be displayed on the display unit 16 after the shear wave velocity is converted into the elastic modulus from a relationship of Expression (10) (E is an elastic modulus and ρ is a density of a medium). A display method will be described in detail in a third embodiment.

$$E=3\rho V_s^2 \quad \text{[Equation 10]}$$

As described above, according to the first embodiment, since the filter is generated after the main component direction of the power spectrum in the k-f plane is rotated by the angle $\alpha$, a filter has a high velocity resolution can be generated. Therefore, since the main component can be extracted with high accuracy by the filter processing, the effect of improving the calculation (measurement) accuracy of the velocity of the main component can be obtained.

Second Embodiment

In the first embodiment described above, as shown in the flow of FIG. 2, a filter is generated for each depth $Z_i$, and the rotation angle $\alpha$ is obtained. The method allows adaptive and accurate processing, but a calculation amount is large and processing takes time.

Therefore, in a second embodiment, using a fact that a range of the shear wave velocity is known to some extent according to a target organ, a filter and a rotation angle $\alpha$ are calculated in advance based on the range of the velocity and stored in the memory, and as shown in FIG. 21, in step 2103, the main component extraction unit 33 reads out and uses the filter and the rotation angle. At this time, the filters having the same shapes and the same rotation angles $\alpha$ are applied at all depths $Z_i$. Accordingly, in the second embodiment, high-speed processing can be implemented. Steps 2101 to 2112 other than step 2103 in FIG. 21 are similar to the respective steps in FIG. 2, and a description thereof will be omitted.

FIG. 22 is a flow showing processing from when the filter generation unit 32 calculates the filter and the rotation angle α in advance to when the filter and the rotation angle α are stored in the memory.

First, in step 2201 of FIG. 22, the filter generation unit 32 specifies a velocity range (maximum velocity $V_H$ and minimum velocity $V_L$) of the shear wave depending on the target organ, a disease, or the like. The velocity range may be specified by a user, or may be automatically determined from a type of the connected probe 10 or the RF signal.

Next, in step 2202 in FIG. 22, the filter generation unit 32 calculates a center angle $\theta_{center}$ on the power spectrum in the k-f plane, for example, using Equation (11).

$$\theta_{center} = \arctan\left(\frac{V_L + V_H}{2}\right) \quad \text{[Equation 11]}$$

Next, in step 2203, the filter generation unit 32 sets a rotation angle $\theta_R$ of the filter. $\theta_R$ is changed in a range of $-\pi/2$ to $+\pi/2$. Next, in step 2204, the filter generation unit 32 generates a filter by using angles $\alpha_L$ and $\alpha_H$ corresponding to the predetermined velocity range of the filter, as shown in FIG. 23.

In step 2205, the filter generation unit 32 calculates a cost function $\Psi_{filter}$ by Equation (12) (see FIG. 24).

$$\Psi_{filter} = H(k,f) \cdot Q(k,f) \quad \text{[Equation 12]}$$

Wherein, H(k, f) represents the generated filter, and Q(k, f) represents, for example, an absolute value distribution of the velocity gradient shown in FIG. 14A.

When the absolute value distribution of the velocity gradient is used as Q(k, f), in step 2207, the filter generation unit 32 sets the angle $\theta_R$ at which the cost function $\Psi_{filter}$ is minimum as the center angle $\theta_0$ after the rotation. Next, in step 2208, the rotation angle α is determined by Equation (13).

$$\alpha = \theta_R - \theta_0 \quad \text{[Equation 13]}$$

The rotation angle α is determined by Equation (13). Next, in step 2209, a filter having the center angle $\theta_0$ determined by using a cost function of Expression (12) is generated.

In step 2210, these filters and rotation angles are stored in the memory.

In this way, in the second embodiment, the filter and the rotation angle α are calculated in advance and stored in the memory, and the main component extraction unit 33 reads out and uses the filter and the rotation angle α in step 2103. Therefore, the calculation amount during velocity measurement can be reduced, and the velocity of the main component can be calculated quickly and accurately with a small calculation amount.

Third Embodiment

In the first embodiment and the second embodiment, a display example on the display unit 16 in FIG. 1 is shown in FIGS. 25 and 26.

In FIG. 25, a B mode image and elasticity map 2501 is displayed on the display unit of the device. The elasticity map is displayed in an ROI 2502 specified by the user. Further, a measured elastic modulus may be displayed as a numerical value on a part of the display unit.

In addition, in the display example in FIG. 25, a gradient distribution 2503 of a wavefront of the shear wave before processing and a gradient distribution 2504 of a wavefront of the main component of the shear wave after processing according to a processing method of the first embodiment or the second embodiment are displayed. The user can confirm the effect of the processing according to the first embodiment or second embodiment by comparing the gradient distribution of the wavefront before and after the processing.

FIG. 26 displays the B mode image and elasticity map 2501 as in FIG. 25. In addition, in FIG. 26, a histogram of a velocity in the ROI 2502 is displayed. By comparing the histograms before and after the processing according to the processing method of the first embodiment or the second embodiment, the effect of the processing can be confirmed.

In FIG. 27, input screen areas 2701 to 2703 in which the user inputs the velocity range is displayed on the display unit of the device.

A button for selecting whether to apply a filter is displayed in the screen area 2701. When the button is turned on, the shear wave velocity is measured by applying the filter.

Further, a screen for receiving a manual specification of the maximum velocity and the minimum velocity in the filter is displayed in the screen area 2702. When the user inputs the maximum velocity and the minimum velocity in the area, corresponding filter processing is performed.

A screen for receiving a selection of an organ and a disease in order to automatically specify the maximum velocity and the minimum velocity to be extracted by the filter is displayed in the screen area 2703. In this area, organs and disease names are displayed, and the user can select an organ and a disease to be diagnosed.

A velocity range suitable for a selectable organ and disease is determined in advance, and is stored in a memory in a device in a table format or the like as shown in FIG. 28. The filter generation unit 32 calls the velocity range from the table or the like according to the organ and the disease selected by the user, generates a filter according to the velocity range, and performs filter processing using the filter.

REFERENCE SIGN LIST

10: probe
13: external input device
16: display unit
20: transmission and reception control unit
21: transmission beamformer
22: reception beamformer
30: control unit
31: measurement unit
32: filter generation unit
33: main component extraction unit
34: velocity calculation unit
35: image generation unit
100: test object
300: ROI
301: first ultrasonic wave
302: second ultrasonic wave
303: shear wave
304: measurement point
401: direction of radiation pressure
402: reflected, refracted, and diffracted wave
403: main component
404: ROI
501: power spectrum in k-f plane
502: filter
601: constant velocity line 602: gradient vector
604, 605: mesh
701: power spectrum in k-f plane after rotation
901: peak value of displacement
1101: projection energy distribution
1102: search range
2001: measurement range
2002: peak time
2003: linear regression line
2501: B image+elasticity map or shear wave velocity map
2502: ROI
2503: gradient distribution of wavefront of shear wave before processing
2504: gradient distribution of wavefront of shear wave after processing
2505: measurement value
2601: histogram of shear wave velocity

The invention claimed is:

1. An ultrasonic diagnostic device, comprising:
a probe including a plurality of vibrating elements;
a transmission beamformer coupled to the probe that generates a transmission signal transmitted to each vibrator element of the probe to generate an ultrasonic wave;
a reception beamformer coupled to the probe that generates a reception signal for a predetermined point in a test object based on a reflected wave received by the probe;
a processor coupled to the transmission beamformer and the reception beamformer;
a memory coupled to the processor, the memory storing instructions that when executed by the processor configure the processor to:
calculate time change data of a displacement of a tissue due to a shear wave generated in the test object from the reception signal,
extract spectrum data in a predetermined region by converting the time change data of the displacement into spectrum data indicating a displacement distribution in a frequency space having a spatial frequency and a time frequency as two respective axes,
rotate the spectrum data by a predetermined angle in the frequency space,
generate a filter that extracts the spectrum data by determining a predetermined angle range around a direction where the displacement shows a peak value in the frequency space and determining an extraction radius of the filter,
filter the spectrum data in the frequency space to extract the spectrum data in the predetermined region by filtering the rotated spectrum data with the generated filter, and
calculate a velocity of the shear wave based on the spectrum data in the extracted predetermined region.

2. The ultrasonic diagnostic device according to claim 1, wherein the extracted spectrum data in the predetermined region is data of a main component of the shear wave.

3. The ultrasonic diagnostic device according to claim 1, wherein the processor is configured to move the extracted spectrum data in the predetermined region to a region where a velocity resolution is high in the frequency space by rotating the spectrum data.

4. The ultrasonic diagnostic device according to claim 1, wherein the processor is configured to rotate the spectrum data in a direction where data of a peak value of the displacement in the spectrum data approaches a spatial frequency axis with a center of the frequency space as a rotation center.

5. The ultrasonic diagnostic device according to claim 4, wherein the processor is configured to calculate a position of the data of the peak value of the displacement in the spectrum data.

6. The ultrasonic diagnostic device according to claim 1, wherein the processor is configured to calculate a velocity gradient based on the calculated velocity of the shear wave in the frequency space.

7. A signal processing device, comprising:
a memory coupled to a processor, the memory storing instructions that when executed by the processor, configure the processor to:
extract spectrum data in a predetermined region by transmitting an ultrasonic wave to an test object where a shear wave is propagating, convert time change data of a displacement obtained from a reception signal of a received reflected wave into the spectrum data indicating a displacement distribution in a frequency space having a spatial frequency and a time frequency as two respective axes,
rotate the spectrum data by a predetermined angle in the frequency space,
generate a filter that extracts the spectrum data by determining a predetermined angle range around a direction where the displacement shows a peak value in the frequency space and determining an extraction radius of the filter,
filter the spectrum data in the frequency space to extract the spectrum data in the predetermined region by filtering the rotated spectrum data with the generated filter, and
calculate a velocity of the shear wave based on the spectrum data in the extracted predetermined region.

8. A non-transitory computer readable medium, storing a program therein, the program causing a computer to execute steps comprising:
extracting spectrum data in a predetermined region by converting time change data of a displacement of a tissue of an test object where a shear wave is propagating into spectrum data indicating a displacement distribution in a frequency space having a spatial frequency and a time frequency as two respective axes,
rotating the spectrum data by a predetermined angle in the frequency space,
generating a filter that extracts the spectrum data by determining a predetermined angle range around a direction where the displacement shows a peak value in the frequency space and determining an extraction radius of the filter,
filtering the spectrum data in the frequency space to extract the spectrum data in the predetermined region by filtering the rotated spectrum data with the generated filter, and
calculating a velocity of the shear wave based on the spectrum data in the extracted predetermined region.

* * * * *